(12) United States Patent
Kranewitter et al.

(10) Patent No.: US 8,399,652 B2
(45) Date of Patent: Mar. 19, 2013

(54) PRIMERS AND PROBES FOR DETECTING GENITAL HPV GENOTYPES

(75) Inventors: Wolfgang Kranewitter, Linz (AT); Christian Mittermayr, Walding (AT); Florian Winner, Hagenberg (AT); Thomas Iftner, Hirrlingen (DE)

(73) Assignee: Greiner Bio-One GmbH, Frickenhausen (DE)

( * ) Notice: Subject to any disclaimer, the term of this patent is extended or adjusted under 35 U.S.C. 154(b) by 894 days.

(21) Appl. No.: 10/582,393

(22) PCT Filed: Dec. 7, 2004

(86) PCT No.: PCT/EP2004/013879
§ 371 (c)(1),
(2), (4) Date: Dec. 26, 2006

(87) PCT Pub. No.: WO2005/056839
PCT Pub. Date: Jun. 23, 2005

(65) Prior Publication Data
US 2008/0287318 A1   Nov. 20, 2008

(30) Foreign Application Priority Data
Dec. 10, 2003   (DE) .................... 103 57 677

(51) Int. Cl.
*C07H 21/04*   (2006.01)
*C12Q 1/68*   (2006.01)
(52) U.S. Cl. .............. 536/24.3; 435/6.11; 435/6.12
(58) Field of Classification Search .............. None
See application file for complete search history.

(56) References Cited

U.S. PATENT DOCUMENTS

| 2001/0006800 | A1* | 7/2001 | Walkerpeach et al. | 435/91.1 |
| 2002/0155113 | A1* | 10/2002 | Chun et al. | 424/146.1 |
| 2002/0155446 | A1* | 10/2002 | Engert et al. | 435/6 |
| 2003/0170268 | A1* | 9/2003 | Neefe et al. | 424/201.1 |
| 2003/0175761 | A1* | 9/2003 | Sabath et al. | 435/6 |
| 2003/0186296 | A1* | 10/2003 | Fodor et al. | 435/6 |

FOREIGN PATENT DOCUMENTS

| WO | WO 0050643 A2 * | 8/2000 |
| WO | WO 01/68915 A1 | 9/2001 |
| WO | WO 03/014382 A2 | 2/2003 |
| WO | WO 03/027323 A1 | 4/2003 |
| WO | WO 03/087829 A2 | 10/2003 |

OTHER PUBLICATIONS

GenBank GI:60955 [online] Jul. 6, 1989 [retrieved on Jul. 3, 2010] retrieved from: http://www.ncbi.nlm.nih.gov/sviewer/viewer.fcgi?val=60955&sat=OLDID&satkey=34726.*
Maas et al. Identification and characterization of a human tRNA-specific adenosine deaminase related to the ADAR family of pre-mRNA editing enzymes. PNAS 96:8895-8900, Aug. 1999.*
Chen et al. Analysis of deletion of the integrated human papillomavirus 16 sequence in cervical cancer: a rapid multiplex polymerase chain reaction. J. Med. Virol. 44(2), Oct. 1994 (abstract).*
Kalantari et al. Disruption of the E1 and E2 reading frames of HPV 16 in cervical carcinoma is associated with poor prognosis. International Journal of Gynecological Pathology 17(2), Apr. 1998 (abstract).*
International Preliminary Report on Patentability for PCT/EP2004/013879, Applicant: Greiner Bio-One GMBH, Form PCT/IPEA/409, dated Nov. 11, 2006 (33 pages).
Doorbar, John, "The Papillomavirus Life Cycle", Journal of Clinical Virology, 32S (2005) S7-S15, Dec. 3, 2004.
European Search Report for EP Patent Application No. 09002019.9-2405 / 12062983, Applicant: Greiner Bio-One GmbH, dated Jul. 15, 2009 (7 pages).
Klaassen, Come H. W., "DNA Microarray Format for Detection and Subtyping of Human Papillomavirus", Journal of Clinical Microbiology, vol. 42, No. 5 (2004), Dec. 30, 2003.

* cited by examiner

*Primary Examiner* — Samuel Woolwine
(74) *Attorney, Agent, or Firm* — Vista IP Law Group LLP

(57) ABSTRACT

The invention relates to oligonucleotides, which are suited as primers for amplifying DNA of genital human papilloma viruses (HPV), to oligonucleotides, which are suited for use as probes for typifying genital HPV genotypes, to methods for amplifying the DNA of genital human papilloma viruses (HPV), to methods for detecting and/or identifying genital HPV genotypes, to nucleotide microarrays containing the oligonucleotides, to kits and to the use of the oligonucleotides for amplifying or typifying genital HPV genotypes, for the diagnosis and/or early diagnosis of diseases and for producing agents for diagnosing diseases.

33 Claims, 5 Drawing Sheets

1A  1B

Figure 1:
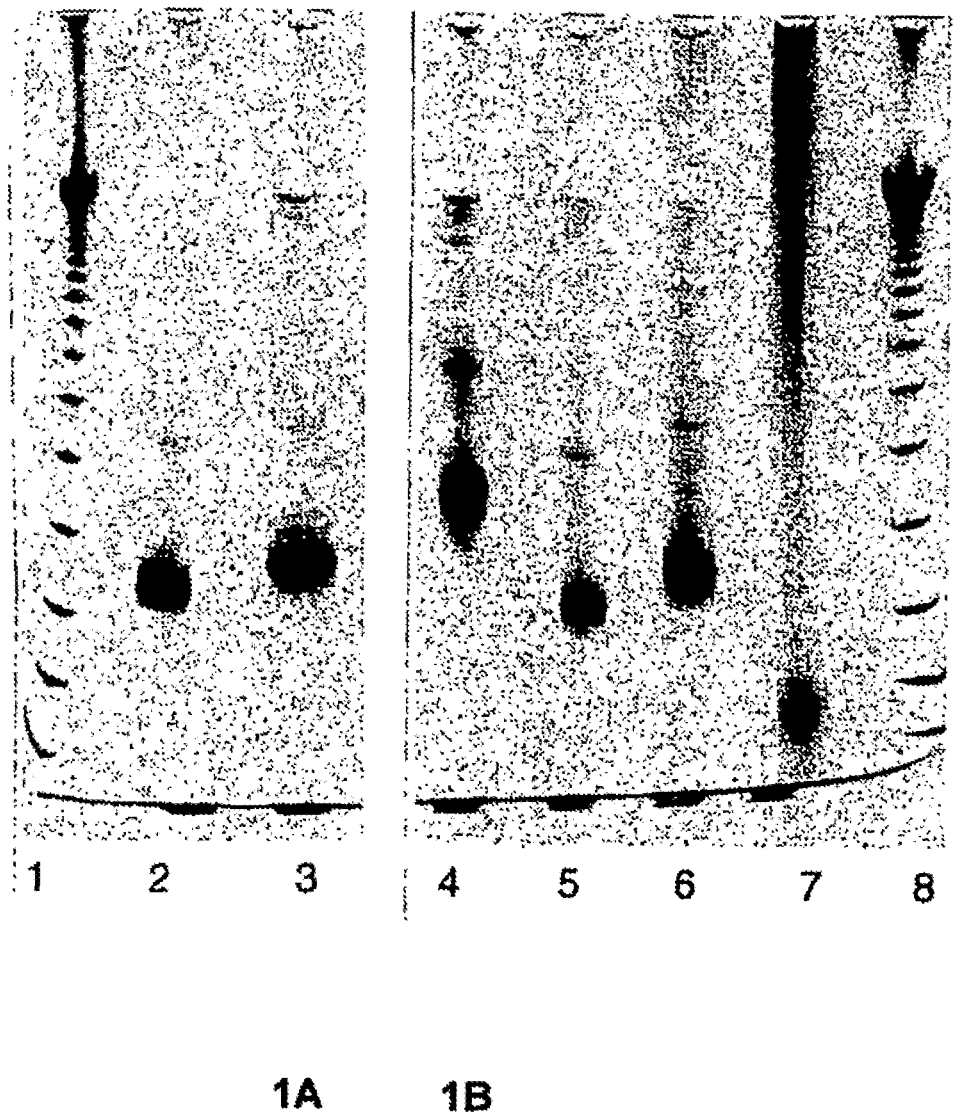

| OC | OC | OC | OC | OC | AC | AC | AC | AC | AC |
|---|---|---|---|---|---|---|---|---|---|
| 6 | 6 | 6 | 6 | 6 | 45 | 45 | 45 | 45 | 45 |
| 11 | 11 | 11 | 11 | 11 | 51 | 51 | 51 | 51 | 51 |
| 16 | 16 | 16 | 16 | 16 | 52 | 52 | 52 | 52 | 52 |
| 18 | 18 | 18 | 18 | 18 | 53 | 53 | 53 | 53 | 53 |
| 31 | 31 | 31 | 31 | 31 | 56 | 56 | 56 | 56 | 56 |
| 33 | 33 | 33 | 33 | 33 | 58 | 58 | 58 | 58 | 58 |
| 35 | 35 | 35 | 35 | 35 | 59 | 59 | 59 | 59 | 59 |
| 39 | 39 | 39 | 39 | 39 | 66 | 66 | 66 | 66 | 66 |
| 40 | 40 | 40 | 40 | 40 | 68 | 68 | 68 | 68 | 68 |
| 42 | 42 | 42 | 42 | 42 | 70 | 70 | 70 | 70 | 70 |
| 43 | 43 | 43 | 43 | 43 | 73 | 73 | 73 | 73 | 73 |
| 44 | 44 | 44 | 44 | 44 | 82 | 82 | 82 | 82 | 82 |
| HC | HC | HC | HC | HC | SC | SC | SC | SC | SC |

OC    Orientation control
HC    Hybridization control
AC    Amplification control (= PCR control)
SC    Sample control

Figure 4a

SEQUENCE LISTING

<160> NUMBER OF SEQ ID NOS: 137

<210> SEQ ID NO 1
<211> LENGTH: 25
<212> TYPE: DNA
<213> ORGANISM: Human papillomavirus
<220> FEATURE:
<221> NAME/KEY: misc_feature
<222> LOCATION: (6)..(6)
<223> OTHER INFORMATION: n is a, c, g, or t

<400> SEQUENCE: 1
cargcnaaaw wwktdaarga ytgtg                                    25

<210> SEQ ID NO 2
<211> LENGTH: 25
<212> TYPE: DNA
<213> ORGANISM: Human papillomavirus
<220> FEATURE:
<221> NAME/KEY: misc_feature
<223> OTHER INFORMATION: r is a or g; k is t or g; n is a, t, g, or c
<220> FEATURE:
<221> NAME/KEY: misc_feature
<222> LOCATION: (6)..(6)
<223> OTHER INFORMATION: n is a, c, g, or t

<400> SEQUENCE: 2
cargcnaaat atktraaaga ttgtg                                    25

<210> SEQ ID NO 3
<211> LENGTH: 25
<212> TYPE: DNA
<213> ORGANISM: Human papillomavirus
<220> FEATURE:
<221> NAME/KEY: misc_feature
<223> OTHER INFORMATION: r is a or g; w is t or a

<400> SEQUENCE: 3
cargcaaaat atgtwaagga ttgtg                                    25

<210> SEQ ID NO 4
<211> LENGTH: 25
<212> TYPE: DNA
<213> ORGANISM: Human papillomavirus
<220> FEATURE:
<221> NAME/KEY: misc_feature
<223> OTHER INFORMATION: r is a or g; w is t or a

<400> SEQUENCE: 4
cargcwaaaa ttgtaaarga ttgtg                                    25

<210> SEQ ID NO 5
<211> LENGTH: 25
<212> TYPE: DNA
<213> ORGANISM: Human papillomavirus

<400> SEQUENCE: 5
caagcaaaaa tagtaaarga ctgtg                                    25

<210> SEQ ID NO 6
<211> LENGTH: 25
<212> TYPE: DNA
<213> ORGANISM: Human papillomavirus

<400> SEQUENCE: 6
cargcaaaat atgtaaaaga ctgtg                                    25

```
<210> SEQ ID NO 7
<211> LENGTH: 23
<212> TYPE: DNA
<213> ORGANISM: Human papillomavirus

<400> SEQUENCE: 7
aryggytsya rccaaaartg rct                                              23

<210> SEQ ID NO 8
<211> LENGTH: 30
<212> TYPE: DNA
<213> ORGANISM: Human papillomavirus

<400> SEQUENCE: 8
aagctttcta ggaggtacag ttattagtca                                       30

<210> SEQ ID NO 9
<211> LENGTH: 30
<212> TYPE: DNA
<213> ORGANISM: Human papillomavirus

<400> SEQUENCE: 9
ataaaacata ggggttctaa aatagaaggc                                       30

<210> SEQ ID NO 10
<211> LENGTH: 30
<212> TYPE: DNA
<213> ORGANISM: Human papillomavirus

<400> SEQUENCE: 10
actaaagttg acagtgtagg taactggaag                                       30

<210> SEQ ID NO 11
<211> LENGTH: 30
<212> TYPE: DNA
<213> ORGANISM: Human papillomavirus

<400> SEQUENCE: 11
ttaaacaatg gattaagtat aggggtacta                                       30

<210> SEQ ID NO 12
<211> LENGTH: 30
<212> TYPE: DNA
<213> ORGANISM: Human papillomavirus

<400> SEQUENCE: 12
aaaagatgtc tattaaacaa tggattaagt                                       30

<210> SEQ ID NO 13
<211> LENGTH: 29
<212> TYPE: DNA
<213> ORGANISM: Human papillomavirus

<400> SEQUENCE: 13
gggtactaaa gttgacagtg taggtaact                                        29

<210> SEQ ID NO 14
<211> LENGTH: 30
<212> TYPE: DNA
<213> ORGANISM: Human papillomavirus

<400> SEQUENCE: 14
gggaacagtt attagttatg ttaattcctg                                       30
```

<210> SEQ ID NO 15
<211> LENGTH: 30
<212> TYPE: DNA
<213> ORGANISM: Human papillomavirus

<400> SEQUENCE: 15
aattgtatag ccattgtagg gccacctgac                                30

<210> SEQ ID NO 16
<211> LENGTH: 30
<212> TYPE: DNA
<213> ORGANISM: Human papillomavirus

<400> SEQUENCE: 16
gggccacctg acactgggaa gtcgtgcttt                                30

<210> SEQ ID NO 17
<211> LENGTH: 30
<212> TYPE: DNA
<213> ORGANISM: Human papillomavirus

<400> SEQUENCE: 17
gggccacctg acactgggaa gtcgtgcttt                                30

<210> SEQ ID NO 18
<211> LENGTH: 30
<212> TYPE: DNA
<213> ORGANISM: Human papillomavirus

<400> SEQUENCE: 18
tgatggaggt gattggaagc aaattgttat                                30

<210> SEQ ID NO 19
<211> LENGTH: 30
<212> TYPE: DNA
<213> ORGANISM: Human papillomavirus

<400> SEQUENCE: 19
tgaaatttct gcaagggtct gtaatatgtt                                30

<210> SEQ ID NO 20
<211> LENGTH: 30
<212> TYPE: DNA
<213> ORGANISM: Human papillomavirus

<400> SEQUENCE: 20
atggaggtga ttggaagcaa attgttatgt                                30

<210> SEQ ID NO 21
<211> LENGTH: 30
<212> TYPE: DNA
<213> ORGANISM: Human papillomavirus

<400> SEQUENCE: 21
gaccaatagt gcaattcctg cgataccaac                                30

<210> SEQ ID NO 22
<211> LENGTH: 30
<212> TYPE: DNA
<213> ORGANISM: Human papillomavirus

<400> SEQUENCE: 22
caaacattat aggcgagccc aaaaacgaca                                30

<210> SEQ ID NO 23
<211> LENGTH: 30
<212> TYPE: DNA
<213> ORGANISM: Human papillomavirus

<400> SEQUENCE: 23
tcctgcgata ccaacaaata gagtttataa                                  30

<210> SEQ ID NO 24
<211> LENGTH: 28
<212> TYPE: DNA
<213> ORGANISM: Human papillomavirus

<400> SEQUENCE: 24
ctgcgatacc aacaaataga gtttataa                                    28

<210> SEQ ID NO 25
<211> LENGTH: 30
<212> TYPE: DNA
<213> ORGANISM: Human papillomavirus

<400> SEQUENCE: 25
agaaacgatc tatgtgtatg tcacaatggc                                  30

<210> SEQ ID NO 26
<211> LENGTH: 30
<212> TYPE: DNA
<213> ORGANISM: Human papillomavirus

<400> SEQUENCE: 26
agaagagggc gggtcgtgga aggaaattgc                                  30

<210> SEQ ID NO 27
<211> LENGTH: 30
<212> TYPE: DNA
<213> ORGANISM: Human papillomavirus

<400> SEQUENCE: 27
ggcgggtcgt ggaaggaaat tgccaaattt                                  30

<210> SEQ ID NO 28
<211> LENGTH: 30
<212> TYPE: DNA
<213> ORGANISM: Human papillomavirus

<400> SEQUENCE: 28
gcacagaaac gatctatgtg tatgtcacaa                                  30

<210> SEQ ID NO 29
<211> LENGTH: 30
<212> TYPE: DNA
<213> ORGANISM: Human papillomavirus

<400> SEQUENCE: 29
gtagatgtga caaagttagt gacgaaggtg                                  30

<210> SEQ ID NO 30
<211> LENGTH: 30
<212> TYPE: DNA
<213> ORGANISM: Human papillomavirus

<400> SEQUENCE: 30
tgagccttat tagctttta caaggatgta                                   30

```
<210> SEQ ID NO 31
<211> LENGTH: 30
<212> TYPE: DNA
<213> ORGANISM: Human papillomavirus

<400> SEQUENCE: 31
caaagttagt gacgaaggtg actggaggga                                      30

<210> SEQ ID NO 32
<211> LENGTH: 30
<212> TYPE: DNA
<213> ORGANISM: Human papillomavirus

<400> SEQUENCE: 32
acagttttta aagggtgtg ttatatcatg                                       30

<210> SEQ ID NO 33
<211> LENGTH: 30
<212> TYPE: DNA
<213> ORGANISM: Human papillomavirus

<400> SEQUENCE: 33
gggtgtgtta tatcatgtgt aaattctaaa                                      30

<210> SEQ ID NO 34
<211> LENGTH: 30
<212> TYPE: DNA
<213> ORGANISM: Human papillomavirus

<400> SEQUENCE: 34
aaagggtgtg ttatatcatg tgtaaattct                                      30

<210> SEQ ID NO 35
<211> LENGTH: 30
<212> TYPE: DNA
<213> ORGANISM: Human papillomavirus

<400> SEQUENCE: 35
attacacata gatgtgattt aatagatgat                                      30

<210> SEQ ID NO 36
<211> LENGTH: 30
<212> TYPE: DNA
<213> ORGANISM: Human papillomavirus

<400> SEQUENCE: 36
tttaatgcag tttatgcaag gtgtggttat                                      30

<210> SEQ ID NO 37
<211> LENGTH: 30
<212> TYPE: DNA
<213> ORGANISM: Human papillomavirus

<400> SEQUENCE: 37
tgatttaata gatgatggag gaaactggaa                                      30

<210> SEQ ID NO 38
<211> LENGTH: 30
<212> TYPE: DNA
<213> ORGANISM: Human papillomavirus

<400> SEQUENCE: 38
tgcagtttat gcaaggtgtg gttatttcat                                      30
```

```
<210> SEQ ID NO 39
<211> LENGTH: 30
<212> TYPE: DNA
<213> ORGANISM: Human papillomavirus

<400> SEQUENCE: 39
ttaatagatg atggaggaaa ctggaaacat                                   30

<210> SEQ ID NO 40
<211> LENGTH: 28
<212> TYPE: DNA
<213> ORGANISM: Human papillomavirus

<400> SEQUENCE: 40
aggtggacga tgacggtgac tggaggga                                     28

<210> SEQ ID NO 41
<211> LENGTH: 30
<212> TYPE: DNA
<213> ORGANISM: Human papillomavirus

<400> SEQUENCE: 41
gcatttctta caaggagcta ttatatccta                                   30

<210> SEQ ID NO 42
<211> LENGTH: 30
<212> TYPE: DNA
<213> ORGANISM: Human papillomavirus

<400> SEQUENCE: 42
aaggcaaatg tccatgtctc aatggataaa                                   30

<210> SEQ ID NO 43
<211> LENGTH: 30
<212> TYPE: DNA
<213> ORGANISM: Human papillomavirus

<400> SEQUENCE: 43
tgtaaacatt acaagcgagc acaaaaaagg                                   30

<210> SEQ ID NO 44
<211> LENGTH: 30
<212> TYPE: DNA
<213> ORGANISM: Human papillomavirus

<400> SEQUENCE: 44
agccttatgc atttttttaca gggcacagtt                                  30

<210> SEQ ID NO 45
<211> LENGTH: 30
<212> TYPE: DNA
<213> ORGANISM: Human papillomavirus

<400> SEQUENCE: 45
tatttcatat gtaaactcca ccagccactt                                   30

<210> SEQ ID NO 46
<211> LENGTH: 30
<212> TYPE: DNA
<213> ORGANISM: Human papillomavirus

<400> SEQUENCE: 46
aatttaggtg tagtaaatgt gatgaaggcg                                   30
```

```
<210> SEQ ID NO 47
<211> LENGTH: 27
<212> TYPE: DNA
<213> ORGANISM: Human papillomavirus

<400> SEQUENCE: 47
gaagtgtgat gaaggcgact ggaaacc                                27

<210> SEQ ID NO 48
<211> LENGTH: 30
<212> TYPE: DNA
<213> ORGANISM: Human papillomavirus

<400> SEQUENCE: 48
gaatgagcct gatgcacttt atgcaaggta                             30

<210> SEQ ID NO 49
<211> LENGTH: 30
<212> TYPE: DNA
<213> ORGANISM: Human papillomavirus

<400> SEQUENCE: 49
cctgatgcac tttatgcaag gtacaataat                             30

<210> SEQ ID NO 50
<211> LENGTH: 30
<212> TYPE: DNA
<213> ORGANISM: Human papillomavirus

<400> SEQUENCE: 50
tccatgtgca aacactatag gttagcagaa                             30

<210> SEQ ID NO 51
<211> LENGTH: 30
<212> TYPE: DNA
<213> ORGANISM: Human papillomavirus

<400> SEQUENCE: 51
acaaatgaga cgtatgtcta tgggtgcatg                             30

<210> SEQ ID NO 52
<211> LENGTH: 30
<212> TYPE: DNA
<213> ORGANISM: Human papillomavirus

<400> SEQUENCE: 52
gacgtatgtc tatgggtgca tggataaaac                             30

<210> SEQ ID NO 53
<211> LENGTH: 30
<212> TYPE: DNA
<213> ORGANISM: Human papillomavirus

<400> SEQUENCE: 53
cagtaaattt gaagacacag gaaattggaa                             30

<210> SEQ ID NO 54
<211> LENGTH: 30
<212> TYPE: DNA
<213> ORGANISM: Human papillomavirus

<400> SEQUENCE: 54
ggcactgtaa ttagttatgt aaactccagc                             30
```

```
<210> SEQ ID NO 55
<211> LENGTH: 30
<212> TYPE: DNA
<213> ORGANISM: Human papillomavirus

<400> SEQUENCE: 55
atatgaaaca gtggataaaa tttaggagca                                    30

<210> SEQ ID NO 56
<211> LENGTH: 30
<212> TYPE: DNA
<213> ORGANISM: Human papillomavirus

<400> SEQUENCE: 56
acgccaaatg aatatgtctc aatggattaa                                    30

<210> SEQ ID NO 57
<211> LENGTH: 30
<212> TYPE: DNA
<213> ORGANISM: Human papillomavirus

<400> SEQUENCE: 57
cgccaaatga atatgtctca atggattaaa                                    30

<210> SEQ ID NO 58
<211> LENGTH: 30
<212> TYPE: DNA
<213> ORGANISM: Human papillomavirus

<400> SEQUENCE: 58
tttaagggca ctaaaggaat ttcttaaagg                                    30

<210> SEQ ID NO 59
<211> LENGTH: 30
<212> TYPE: DNA
<213> ORGANISM: Human papillomavirus

<400> SEQUENCE: 59
ggtgcaataa tatcatttgt aaattcaaac                                    30

<210> SEQ ID NO 60
<211> LENGTH: 30
<212> TYPE: DNA
<213> ORGANISM: Human papillomavirus

<400> SEQUENCE: 60
ggcactaaag gaatttctta aaggaacacc                                    30

<210> SEQ ID NO 61
<211> LENGTH: 30
<212> TYPE: DNA
<213> ORGANISM: Human papillomavirus

<400> SEQUENCE: 61
agggcactaa aggaatttct taaggaaca                                     30

<210> SEQ ID NO 62
<211> LENGTH: 30
<212> TYPE: DNA
<213> ORGANISM: Human papillomavirus

<400> SEQUENCE: 62
cattatctat gtcagcctgg ataaggtata                                    30
```

<210> SEQ ID NO 63
<211> LENGTH: 30
<212> TYPE: DNA
<213> ORGANISM: Human papillomavirus

<400> SEQUENCE: 63
gcacaaagaa aatcattatc tatgtcagcc                                    30

<210> SEQ ID NO 64
<211> LENGTH: 30
<212> TYPE: DNA
<213> ORGANISM: Human papillomavirus

<400> SEQUENCE: 64
aaatcattat ctatgtcagc ctggataagg                                    30

<210> SEQ ID NO 65
<211> LENGTH: 30
<212> TYPE: DNA
<213> ORGANISM: Human papillomavirus

<400> SEQUENCE: 65
aaacatatga atattggaca atggatacag                                    30

<210> SEQ ID NO 66
<211> LENGTH: 30
<212> TYPE: DNA
<213> ORGANISM: Human papillomavirus

<400> SEQUENCE: 66
gaaagaaaac atatgaatat tggacaatgg                                    30

<210> SEQ ID NO 67
<211> LENGTH: 30
<212> TYPE: DNA
<213> ORGANISM: Human papillomavirus

<400> SEQUENCE: 67
ttaattaggt tcttaagtgg atgtgtaata                                    30

<210> SEQ ID NO 68
<211> LENGTH: 30
<212> TYPE: DNA
<213> ORGANISM: Human papillomavirus

<400> SEQUENCE: 68
taaagcatgt atgtagcaag gtggatgatg                                    30

<210> SEQ ID NO 69
<211> LENGTH: 30
<212> TYPE: DNA
<213> ORGANISM: Human papillomavirus

<400> SEQUENCE: 69
gatgaatatg aaacaatgga taaagcatgt                                    30

<210> SEQ ID NO 70
<211> LENGTH: 30
<212> TYPE: DNA
<213> ORGANISM: Human papillomavirus

<400> SEQUENCE: 70
aagcatgtat gtagcaaggt ggatgatggt                                    30

```
<210> SEQ ID NO 71
<211> LENGTH: 30
<212> TYPE: DNA
<213> ORGANISM: Human papillomavirus

<400> SEQUENCE: 71
gttatttatg gtcctccaaa cacgggtaaa                                   30

<210> SEQ ID NO 72
<211> LENGTH: 30
<212> TYPE: DNA
<213> ORGANISM: Human papillomavirus

<400> SEQUENCE: 72
aaacaatgga taaagcatgt atgtagcaag                                   30

<210> SEQ ID NO 73
<211> LENGTH: 30
<212> TYPE: DNA
<213> ORGANISM: Human papillomavirus

<400> SEQUENCE: 73
ttagttattt atggtcctcc aaacacgggt                                   30

<210> SEQ ID NO 74
<211> LENGTH: 30
<212> TYPE: DNA
<213> ORGANISM: Human papillomavirus

<400> SEQUENCE: 74
ttagcttttt aggaggtgta gtgctatcat                                   30

<210> SEQ ID NO 75
<211> LENGTH: 30
<212> TYPE: DNA
<213> ORGANISM: Human papillomavirus

<400> SEQUENCE: 75
ttgtgattta gtagaggagg aaggtgagtg                                   30

<210> SEQ ID NO 76
<211> LENGTH: 30
<212> TYPE: DNA
<213> ORGANISM: Human papillomavirus

<400> SEQUENCE: 76
cgttgtgatt tagtagagga ggaaggtgag                                   30

<210> SEQ ID NO 77
<211> LENGTH: 30
<212> TYPE: DNA
<213> ORGANISM: Human papillomavirus

<400> SEQUENCE: 77
catcgttgtg atttagtaga ggaggaaggt                                   30

<210> SEQ ID NO 78
<211> LENGTH: 30
<212> TYPE: DNA
<213> ORGANISM: Human papillomavirus

<400> SEQUENCE: 78
gggcacaaca gcaacaaatg aatatgtgcc                                   30
```

```
<210> SEQ ID NO 79
<211> LENGTH: 30
<212> TYPE: DNA
<213> ORGANISM: Human papillomavirus

<400> SEQUENCE: 79
cacaacagca acaaatgaat atgtgccagt                                          30

<210> SEQ ID NO 80
<211> LENGTH: 30
<212> TYPE: DNA
<213> ORGANISM: Human papillomavirus

<400> SEQUENCE: 80
ctgtttggta ctttgtggac cgccaaatac                                          30

<210> SEQ ID NO 81
<211> LENGTH: 30
<212> TYPE: DNA
<213> ORGANISM: Human papillomavirus

<400> SEQUENCE: 81
tttcaagggt ctgtcatttc atttgtgaat                                          30

<210> SEQ ID NO 82
<211> LENGTH: 30
<212> TYPE: DNA
<213> ORGANISM: Human papillomavirus

<400> SEQUENCE: 82
acatttttta aaaggatgca ttatttcata                                          30

<210> SEQ ID NO 83
<211> LENGTH: 30
<212> TYPE: DNA
<213> ORGANISM: Human papillomavirus

<400> SEQUENCE: 83
cgtggtatga caatgggaca atggatacaa                                          30

<210> SEQ ID NO 84
<211> LENGTH: 30
<212> TYPE: DNA
<213> ORGANISM: Human papillomavirus

<400> SEQUENCE: 84
gagcagaaaa gcgtggtatg acaatgggac                                          30

<210> SEQ ID NO 85
<211> LENGTH: 30
<212> TYPE: DNA
<213> ORGANISM: Human papillomavirus

<400> SEQUENCE: 85
aggatgcatt atttcatatg taaattccaa                                          30

<210> SEQ ID NO 86
<211> LENGTH: 30
<212> TYPE: DNA
<213> ORGANISM: Human papillomavirus

<400> SEQUENCE: 86
aaagcgtggt atgacaatgg gacaatggat                                          30
```

<210> SEQ ID NO 87
<211> LENGTH: 30
<212> TYPE: DNA
<213> ORGANISM: Human papillomavirus

<400> SEQUENCE: 87
agcctgctac attttttaca aggaactgta                                        30

<210> SEQ ID NO 88
<211> LENGTH: 30
<212> TYPE: DNA
<213> ORGANISM: Human papillomavirus

<400> SEQUENCE: 88
gattacacat agaggccgca aggtggcaga                                        30

<210> SEQ ID NO 89
<211> LENGTH: 30
<212> TYPE: DNA
<213> ORGANISM: Human papillomavirus

<400> SEQUENCE: 89
attacacata gaggccgcaa ggtggcagac                                        30

<210> SEQ ID NO 90
<211> LENGTH: 30
<212> TYPE: DNA
<213> ORGANISM: Human papillomavirus

<400> SEQUENCE: 90
agtggattac acatagaggc cgcaaggtgg                                        30

<210> SEQ ID NO 91
<211> LENGTH: 30
<212> TYPE: DNA
<213> ORGANISM: Human papillomavirus

<400> SEQUENCE: 91
acagtggatt acacatagag gccgcaaggt                                        30

<210> SEQ ID NO 92
<211> LENGTH: 30
<212> TYPE: DNA
<213> ORGANISM: Human papillomavirus

<400> SEQUENCE: 92
gtaccattta ttagtgccct taaattgttt                                        30

<210> SEQ ID NO 93
<211> LENGTH: 30
<212> TYPE: DNA
<213> ORGANISM: Human papillomavirus

<400> SEQUENCE: 93
ttacggacca agcgacacag ggaagtcgct                                        30

<210> SEQ ID NO 94
<211> LENGTH: 30
<212> TYPE: DNA
<213> ORGANISM: Human papillomavirus

<400> SEQUENCE: 94
tacggaccaa gcgacacagg gaagtcgcta                                        30

```
<210> SEQ ID NO 95
<211> LENGTH: 30
<212> TYPE: DNA
<213> ORGANISM: Human papillomavirus

<400> SEQUENCE: 95
gagccttata aattttttcc aagggtcagt                                    30

<210> SEQ ID NO 96
<211> LENGTH: 30
<212> TYPE: DNA
<213> ORGANISM: Human papillomavirus

<400> SEQUENCE: 96
ccttataaat ttttccaag ggtcagtcat                                     30

<210> SEQ ID NO 97
<211> LENGTH: 30
<212> TYPE: DNA
<213> ORGANISM: Human papillomavirus

<400> SEQUENCE: 97
attacaaaag ggcacagcaa cagcaaatga                                    30

<210> SEQ ID NO 98
<211> LENGTH: 30
<212> TYPE: DNA
<213> ORGANISM: Human papillomavirus

<400> SEQUENCE: 98
atggaggaga ctggagaaca atagtaaagc                                    30

<210> SEQ ID NO 99
<211> LENGTH: 30
<212> TYPE: DNA
<213> ORGANISM: Human papillomavirus

<400> SEQUENCE: 99
aagttgtatg gtaatatgcg gaccaccaaa                                    30

<210> SEQ ID NO 100
<211> LENGTH: 30
<212> TYPE: DNA
<213> ORGANISM: Human papillomavirus

<400> SEQUENCE: 100
caaggatgtg taatatcata tgtaaacgcc                                    30

<210> SEQ ID NO 101
<211> LENGTH: 30
<212> TYPE: DNA
<213> ORGANISM: Human papillomavirus

<400> SEQUENCE: 101
aggagactgg agaacaatag taaagctatt                                    30

<210> SEQ ID NO 102
<211> LENGTH: 30
<212> TYPE: DNA
<213> ORGANISM: Human papillomavirus

<400> SEQUENCE: 102
gttgtatggt aatatgcgga ccaccaaaca                                    30
```

```
<210> SEQ ID NO 103
<211> LENGTH: 30
<212> TYPE: DNA
<213> ORGANISM: Human papillomavirus

<400> SEQUENCE: 103
aacgacaaat gtcaatgccg caatggatta                              30

<210> SEQ ID NO 104
<211> LENGTH: 30
<212> TYPE: DNA
<213> ORGANISM: Human papillomavirus

<400> SEQUENCE: 104
cgggcacaaa aacgacaaat gtcaatgccg                              30

<210> SEQ ID NO 105
<211> LENGTH: 30
<212> TYPE: DNA
<213> ORGANISM: Human papillomavirus

<400> SEQUENCE: 105
tcaatgccgc aatggattaa atttagatgc                              30

<210> SEQ ID NO 106
<211> LENGTH: 30
<212> TYPE: DNA
<213> ORGANISM: Human papillomavirus

<400> SEQUENCE: 106
atggcgcaat ggattaggtt tagatgtgat                              30

<210> SEQ ID NO 107
<211> LENGTH: 30
<212> TYPE: DNA
<213> ORGANISM: Human papillomavirus

<400> SEQUENCE: 107
aaatgactat ggcgcaatgg attaggttta                              30

<210> SEQ ID NO 108
<211> LENGTH: 30
<212> TYPE: DNA
<213> ORGANISM: Human papillomavirus

<400> SEQUENCE: 108
attaggttta gatgtgataa atgtgacgat                              30

<210> SEQ ID NO 109
<211> LENGTH: 30
<212> TYPE: DNA
<213> ORGANISM: Human papillomavirus

<400> SEQUENCE: 109
taaatttata caaggtgtag ttatttcgta                              30

<210> SEQ ID NO 110
<211> LENGTH: 30
<212> TYPE: DNA
<213> ORGANISM: Human papillomavirus

<400> SEQUENCE: 110
atgtgattta actaatgatg gtggtaattg                              30
```

<210> SEQ ID NO 111
<211> LENGTH: 30
<212> TYPE: DNA
<213> ORGANISM: Human papillomavirus

<400> SEQUENCE: 111
taatgatggt ggtaattgga aagatattgt                            30

<210> SEQ ID NO 112
<211> LENGTH: 30
<212> TYPE: DNA
<213> ORGANISM: Human papillomavirus

<400> SEQUENCE: 112
taaacaaatg tcaatggcac aatggataca                            30

<210> SEQ ID NO 113
<211> LENGTH: 30
<212> TYPE: DNA
<213> ORGANISM: Human papillomavirus

<400> SEQUENCE: 113
ttaattagat ttttgcaagg gtgcgttatt                            30

<210> SEQ ID NO 114
<211> LENGTH: 30
<212> TYPE: DNA
<213> ORGANISM: Human papillomavirus

<400> SEQUENCE: 114
agaaaatcac taacaatgtc agcatggatt                            30

<210> SEQ ID NO 115
<211> LENGTH: 30
<212> TYPE: DNA
<213> ORGANISM: Human papillomavirus

<400> SEQUENCE: 115
taggtataga tgtgacaaag tgcaagacgg                            30

<210> SEQ ID NO 116
<211> LENGTH: 30
<212> TYPE: DNA
<213> ORGANISM: Human papillomavirus

<400> SEQUENCE: 116
ttgcgatacc agggtattaa ctttatgtat                            30

<210> SEQ ID NO 117
<211> LENGTH: 30
<212> TYPE: DNA
<213> ORGANISM: Human papillomavirus

<400> SEQUENCE: 117
gaggtacagt tattagtcat gtaaattcca                            30

<210> SEQ ID NO 118
<211> LENGTH: 32
<212> TYPE: DNA
<213> ORGANISM: Human papillomavirus

<400> SEQUENCE: 118
taagtttttg gggggaacag ttattagtta tg                         32

```
<210> SEQ ID NO 119
<211> LENGTH: 34
<212> TYPE: DNA
<213> ORGANISM: Human papillomavirus

<400> SEQUENCE: 119
ttatacactt tatacaagga gcagtaatat catt                                  34

<210> SEQ ID NO 120
<211> LENGTH: 30
<212> TYPE: DNA
<213> ORGANISM: Human papillomavirus

<400> SEQUENCE: 120
caaggatgta taatatcata tgcaaattca                                       30

<210> SEQ ID NO 121
<211> LENGTH: 35
<212> TYPE: DNA
<213> ORGANISM: Human papillomavirus

<400> SEQUENCE: 121
tgagtttaat aaacttctta gcaggaactg taata                                 35

<210> SEQ ID NO 122
<211> LENGTH: 30
<212> TYPE: DNA
<213> ORGANISM: Human papillomavirus

<400> SEQUENCE: 122
aggcggtacc atattatcat atgtaaatgc                                       30

<210> SEQ ID NO 123
<211> LENGTH: 30
<212> TYPE: DNA
<213> ORGANISM: Human papillomavirus

<400> SEQUENCE: 123
ggaggcactg taattagtta tgtaaactcc                                       30

<210> SEQ ID NO 124
<211> LENGTH: 30
<212> TYPE: DNA
<213> ORGANISM: Human papillomavirus

<400> SEQUENCE: 124
gagttttata catttcctac aaggtgcaat                                       30

<210> SEQ ID NO 125
<211> LENGTH: 30
<212> TYPE: DNA
<213> ORGANISM: Human papillomavirus

<400> SEQUENCE: 125
tatttgcaat gagcctaatg aagtttatgc                                       30

<210> SEQ ID NO 126
<211> LENGTH: 32
<212> TYPE: DNA
<213> ORGANISM: Human papillomavirus

<400> SEQUENCE: 126
gagtttaatt aggttcttaa gtggatgtgt aa                                    32
```

<210> SEQ ID NO 127
<211> LENGTH: 29
<212> TYPE: DNA
<213> ORGANISM: Human papillomavirus

<400> SEQUENCE: 127
gtttagttat ttatggtcct ccaaacacg                                    29

<210> SEQ ID NO 128
<211> LENGTH: 30
<212> TYPE: DNA
<213> ORGANISM: Human papillomavirus

<400> SEQUENCE: 128
agtcttataa agttttttca agggtctgtc                                   30

<210> SEQ ID NO 129
<211> LENGTH: 32
<212> TYPE: DNA
<213> ORGANISM: Human papillomavirus

<400> SEQUENCE: 129
tgagcctgct acatttttta caaggaactg ta                                32

<210> SEQ ID NO 130
<211> LENGTH: 27
<212> TYPE: DNA
<213> ORGANISM: Human papillomavirus

<400> SEQUENCE: 130
tgagccttat aaattttttc caagggt                                      27

<210> SEQ ID NO 131
<211> LENGTH: 32
<212> TYPE: DNA
<213> ORGANISM: Human papillomavirus

<400> SEQUENCE: 131
atacatttct tgcaaggcac aataatttca ta                                32

<210> SEQ ID NO 132
<211> LENGTH: 30
<212> TYPE: DNA
<213> ORGANISM: Human papillomavirus

<400> SEQUENCE: 132
tgagtcttat acatttcttg caaggcacaa                                   30

<210> SEQ ID NO 133
<211> LENGTH: 30
<212> TYPE: DNA
<213> ORGANISM: Human papillomavirus

<400> SEQUENCE: 133
aatgcacttt ttacaaggta cagtaatttc                                   30

<210> SEQ ID NO 134
<211> LENGTH: 32
<212> TYPE: DNA
<213> ORGANISM: Human papillomavirus

<400> SEQUENCE: 134
ttaaatttat acaaggtgta gttatttcgt at                                32

```
<210> SEQ ID NO 135
<211> LENGTH: 26
<212> TYPE: DNA
<213> ORGANISM: Human papillomavirus

<400> SEQUENCE: 135
taattagatt tttgcaaggg tgcgtt                                          26

<210> SEQ ID NO 136
<211> LENGTH: 25
<212> TYPE: DNA
<213> ORGANISM: Human papillomavirus
<220> FEATURE:
<221> NAME/KEY: misc_feature
<222> LOCATION: (6)..(6)
<223> OTHER INFORMATION: n = inosine

<400> SEQUENCE: 136
cargcnaaaw wwktdaarga ytgtg                                           25

<210> SEQ ID NO 137
<211> LENGTH: 25
<212> TYPE: DNA
<213> ORGANISM: Human papillomavirus
<220> FEATURE:
<221> NAME/KEY: misc_feature
<222> LOCATION: (6)..(6)
<223> OTHER INFORMATION: n = inosine

<400> SEQUENCE: 137
cargcnaaat atktraaaga ttgtg                                           25
```

PRIMERS AND PROBES FOR DETECTING GENITAL HPV GENOTYPES

RELATED APPLICATIONS

This application is a U.S. National Stage filing under 35 U.S.C. §371 of International Application No. PCT/EP2004/013879, filed Dec. 7, 2004, which claims priority to German Patent Application No. 103 57 677.0, filed Dec. 10, 2003. The contents of the aforementioned applications are hereby incorporated herein by reference in their entireties. Priority to the aforementioned applications is hereby expressly claimed in accordance with 35 U.S.C. §§119, 120, 365 and 371 and any other applicable statutes.

FIELD OF THE INVENTION

The present invention relates to oligonucleotides that are suitable for use as primers to amplify the DNA of genital human papilloma viruses (HPVs), oligonucleotides and nucleic acid molecules that can be used as probes for detecting and/or identifying genital HPV genotypes, processes for amplifying the DNA of genital human papilloma viruses, processes for detecting and/or identifying genital HPV genotypes, the nucleotide arrays and kits comprising the oligonucleotides and nucleic acid molecules, as well as the use of the oligonucleotides and nucleic acid molecules for the amplification of or for the detection and/or identification of genital HPV genotypes, for the diagnosis and/or early detection of diseases, as well as for preparing means to diagnose diseases.

BACKGROUND OF THE INVENTION

Infections with the human pathogenic papilloma virus, which is widely distributed among the population, are among the most common sexually transmitted viral diseases. However, it is also possible for newborns to become infected through the birth channel. The consequences of an HPV disease usually involve harmless dermal symptoms. To date, about a hundred different types of this virus have been identified. Papilloma viruses are classified into cutaneous types, which mainly cause keratinizing lesions in the epithelium, and mucosal types, which in particular affect the mucous membranes. The viruses are also classified further into types associated with benign lesions (low-risk types) and types that are associated with preneoplastic and malignant epithelial changes (high-risk types). Known high-risk types are, for example, types 16, 18, 26, 31, 33, 35, 39, 45, 51, 52, 53, 56, 58, 59, 66, 68, 73, and 82. Known low-risk HPV types are, for example, types 6, 11, 40, 42, 53, 54, 57, and MM8.

About 25 papilloma virus types are causally associated with diseases that occur in the female genital area. HPV infections manifest themselves in the female anogenital area, in particular in the form of condylomatous, dysplastic, and neoplastic lesions. Since 99.7% of all cervical cancers contain papilloma virus DNA, it is now generally accepted that human papilloma viruses are undeniable risk factors for the development of this type of cancer. Epidemiological and molecular studies have shown that continuous infection with high-risk HPV types, in particular HPV types 16 and 18, plays a significant role in the development of cervical carcinoma.

Cervical cancer and other cancer diseases that are epidemiologically associated with papilloma viruses, for example certain forms of skin cancer, are preventable diseases if early detection and treatment are assured. A reliable process for diagnosing the presence of an HPV infection is therefore essential to effective therapy.

In diagnostic terms, it is possible to distinguish between three forms of HPV infections: clinical, subclinical, and latent HPV infections. Epithelial changes that are associated with HPV and that occur in the subclinical or clinically manifest stage of the infection can be detected relatively well using cytological techniques. Early stages of cervical cancer therefore are currently identified mainly by taking a cell smear from the portio or cervix in combination with colposcopy. While cytological methods have contributed to a significant decrease in the incidence of cervical carcinomas in recent years, they do not provide completely satisfactory results. It is not possible to obtain a prognosis on the further development of individual lesions. Moreover, the cytological methods suffer from relatively large subjective errors, and they are not standardized.

Since it is not possible to breed and culture HPV, the detection of HPV in the laboratory is accomplished by identifying viral DNA or shell proteins. For example, group-specific antigens (capsid antigens) of the papilloma viruses can be identified by means of immunohistochemical staining. However, this test is rather inconclusive because of its low sensitivity. Serological tests to detect HPV-specific antibodies in the serum of patients are of no importance for diagnostics because in only 50% of all cases can antibodies be detected, even in patients suffering from cervical cancer.

Methods used to detect viral nucleic acids in clinical tissue samples are very important for diagnostics. Particularly important are those methods that allow one to differentiate between individual types of a low-risk and high-risk HPV infection, since only the HPV types HPV16, HPV18, HPV31, HPV33, HPV35, HPV39, HPV45, HPV51, HPV52, HPV56, HPV58, HPV59, HPV66, HPV68, and HPV82 are associated with the development of carcinomas of the cervix in situ, and HPV53 probably is also carcinogenic.

One prior-art method for detecting HPV nucleic acids is the HCM (hybrid capture microplate) method from the Digene company (HC2 HPV DNA test), which is based on a signal-amplifying hybridization method. HPV-specific RNA sequences are used as the hybridization probes. After the probes have been incubated with denatured HPV-DNA from infected tissue, the RNA/DNA hybrids that are formed are captured on the surface of the microplate by means of specific antibodies. The RNA/DNA hybrids are detected by means of a second antibody that is marked with alkaline phosphatase. This enzyme can generate measurable light after the addition of certain substances. The HCM method permits subgroup-specific differentiation between low-risk types 6, 11, 42, 43, and 44 and high-risk types 16, 18, 31, 33, 35, 39, 45, 51, 52, 56, 58, 59, and 68, and therefore can be useful in the differential diagnostics of unclear cytological findings. One disadvantage of this method, though, is that some high-risk types cannot be detected. Moreover, a cross-reaction occurs between the two subgroups.

Many methods for detecting viral nucleic acids in clinical tissue samples that are known in the prior art are based on prior HPV gene amplification. The PCR method has proved to be the most sensitive. By using such methods, a relatively broad spectrum of HPV viruses can be detected and then be typed. This typing is mainly accomplished by means of a sequence analysis of the PCR amplification product. The typing allows the HPV type to be described precisely, not only in the case of individual infections, but also in the case of multiple or mixed infections, so that it provides a means of assessing the oncogenic potential of the detected HPV genotypes that goes beyond cytological findings.

Snijders et al. J. Gen. Virol., 71 (1990), 173 to 181, and Surentheran et al., J. Clin. Path., 51 (1998), 606-610, describe the PCR process for detecting HPV-DNA. In this process, primer pairs that lie within HPV structure gene L1 are used. The amplified gene fragment is then sequenced in order to classify the detected HPV types. A disadvantage of the two methods, however, is that the L1 gene is less well preserved than other areas of the HPV-DNA. Therefore, only a limited number of HPV types can be detected using the methods described above. For example, the primers described by Snijder et al. can only detect some of the HPV types, such as HPV30, HPV39, and HPV51, with greatly reduced sensitivity. In addition, when the primers described by Snijder et al. are used, some HPV types, such as HPV18, result in the formation of additional bands.

DE 100 09 143 A1 describes the PCR process for detecting a general HPV infection, in particular, however, for detecting HPV-DNA in the anogenital area. In this process two primer pairs, which lie within the preserved HPV gene E1, are used. However, only the amplification products that are obtained using one of the primer pairs can be used for reliable typing, but not the amplification products obtained from the second primer pair. Another disadvantage is that the typing is carried out by sequencing the amplification products, or the amplification products have to be studied by means of temperature-gradient gel electrophoresis. Both sequencing and performing a temperature-gradient gel electrophoresis are labor- and cost-intensive procedures.

One significant disadvantage of the prior-art commercial tests for detecting and typing the HPV genotypes mainly is due to the fact that these tests only detect a limited spectrum of HPV types, and, in particular, rare genital HPV types are not adequately detected, even though some of these virus types are known to have a high oncogenic potential. Another disadvantage is that a time- and cost-intensive sequencing must always be performed after the amplification in order to be able to carry out the typing.

SUMMARY OF THE INVENTION

Detailed Description of the Invention

The technical problem upon which the present invention is based involves providing means and methods that permit a fast and reliable detection, and/or a simple and fast typing, in particular of genital high-risk HPV genotypes, and that do not have the disadvantages that are known to be present in the prior art—in other words, in particular to detect all HPV types that are known to be associated with cancerous diseases among women.

The present invention solves the underlying technical problem by providing oligonucleotides that can be used as forward and reverse primers to amplify a nucleic acid area of a genital human papilloma virus (HPV). The present invention solves the underlying technical problem in particular by providing an oligonucleotide that can be used as a forward primer to amplify a nucleic acid area of a genital human papilloma virus (HPV) and that has the sequence 5'-CAR GCI AAA WWW KTD AAR GAY TGT G-3' (SEQ ID no. 136) or 5'-CAR GCN AAA WWW KTD AAR GAY TGT G-3' (SEQ ID no. 1), where R=A or G, W=T or A, K=T or G, I=inosine, N=A, T, G, or C, D=A, T, or G, and Y=C or T.

The oligonucleotide that is used in the invention as the forward primer is preferably selected from the group comprising:

a) an oligonucleotide having the sequence 5'-CAR GCI AAA TAT KTR AAA GAT TGT G-3' (SEQ ID no. 137) or 5'-CAR GCN AAA TAT KTR AAA GAT TGT G-3' (SEQ ID no. 2),
b) an oligonucleotide having the sequence 5'-CAR GCA AAA TAT GTW AAG GAT TGT G-3' (SEQ ID no. 3),
c) an oligonucleotide having the sequence 5'-CAR GCW AAA ATT GTA AAR GAT TGT G-3' (SEQ ID no. 4),
d) an oligonucleotide having the sequence 5'-CAA GCA AAA ATA GTA AAR GAC TGT G-3' (SEQ ID no. 5) and
e) an oligonucleotide having the sequence 5'-CAR GCA AAA TAT GTA AAA GAC TGT G-3' (SEQ ID no. 6), where R=A or G, W=T or A, K=T or G, I=inosine, and N=A, T, G, or C.

In a more preferred embodiment of the invention an equimolar mixture of the oligonucleotides having the nucleotide sequences recited in SEQ ID nos. 2 to 6 is used as the forward primer to amplify the nucleic acid of genital human papilloma viruses.

The present invention also solves the underlying technical problem by providing an oligonucleotide that can be used as a primer, in particular as a reverse primer, to amplify a nucleic acid area of a genital human papilloma virus, wherein the oligonucleotide has the sequence 5'-ARY GGY TSY ARC CM AAR TGR CT-3' (SEQ ID no. 7), where R=A or G, Y=C or T, and S=C or G.

The present invention also solves the underlying technical problem by providing an oligonucleotide that can be used as a probe for detecting and/or identifying genital HPV genotypes and that is selected from the group comprising:

1) an oligonucleotide having the nucleotide sequence recited in SEQ ID nos. 8, 9, or 117 to detect and/or determine the HPV6 genotype, in particular the HPV6b genotype,
2) an oligonucleotide having the nucleotide sequence recited in SEQ ID nos. 10, 11, 12, 13, 14, 15, 16, 17, or 118 to detect and/or identify the HPV11 genotype,
3) an oligonucleotide having the nucleotide sequence recited in SEQ ID nos. 18, 19, or 20 to detect and/or identify the HPV16 genotype,
4) an oligonucleotide having the nucleotide sequence recited in SEQ ID nos. 21, 22, 23, 24, or 119 to detect and/or identify the HPV18 genotype,
5) an oligonucleotide having the nucleotide sequence recited in SEQ ID nos. 25, 26, 27, or 28 to detect and/or identify the HPV26 genotype,
6) an oligonucleotide having the nucleotide sequence recited in SEQ ID nos. 29, 30, 31, or 120 to detect and/or identify the HPV31 genotype,
7) an oligonucleotide having the nucleotide sequence recited in SEQ ID nos. 32, 33, or 34 to detect and/or identify the HPV33 genotype,
8) an oligonucleotide having the nucleotide sequence recited in SEQ ID nos. 35, 36, 37, 38, or 39 to detect and/or identify the HPV34 genotype,
9) an oligonucleotide having the nucleotide sequence recited in SEQ ID nos. 40, or 41 to detect and/or identify the HPV35 genotype, in particular the HPV35h genotype,
10) an oligonucleotide having the nucleotide sequence recited in SEQ ID nos. 42, 43, 44, 45, or 46 to detect and/or identify the HPV39 genotype,
11) an oligonucleotide having the nucleotide sequence recited in SEQ ID nos. 47, 48, 49, or 50 to detect and/or identify the HPV40 genotype,
12) an oligonucleotide having the nucleotide sequence recited in SEQ ID nos. 51, 52, or 121 to detect and/or identify the HPV42 genotype, 13) an oligonucleotide having the nucleotide sequence recited in SEQ ID no. 122 to detect and/or identify the HPV43 genotype,
14) an oligonucleotide having the nucleotide sequence recited in SEQ ID nos. 53, 54, 55, or 123 to detect and/or identify the HPV44 genotype,
15) an oligonucleotide having the nucleotide sequence recited in SEQ ID nos. 56, 57, 58, 59, 60, 61, or 124 to detect and/or identify the HPV45 genotype,
16) an oligonucleotide having the nucleotide sequence recited in SEQ ID nos. 62, 63, 64, or 125 to detect and/or identify the HPV51 genotype,
17) an oligonucleotide having the nucleotide sequence recited in SEQ ID nos. 65, 66, 67, or 126 to detect and/or identify the HPV52 genotype,
18) an oligonucleotide having the nucleotide sequence recited in SEQ ID nos. 68, 69, 70, 71, 72, 73, or 127 to detect and/or identify the HPV53 genotype,
19) an oligonucleotide having the nucleotide sequence recited in SEQ ID nos. 74, 75, 76, or 77 to detect and/or identify the HPV54 genotype,
20) an oligonucleotide having the nucleotide sequence recited in SEQ ID nos. 78, 79, 80, 81, or 128 to detect and/or identify the HPV56 genotype,
21) an oligonucleotide having the nucleotide sequence recited in SEQ ID nos. 82, 83, 84, 85, or 86 to detect and/or identify the HPV58 genotype,
22) an oligonucleotide having the nucleotide sequence recited in SEQ ID nos. 87, or 129 to detect and/or identify the HPV59 genotype,
23) an oligonucleotide having the nucleotide sequence recited in SEQ ID nos. 88, 89, 90, 91, 92, 93, or 94 to detect and/or identify the des HPV61 genotype,
24) an oligonucleotide having the nucleotide sequence recited in SEQ ID nos. 95, 96, 97, or 130 to detect and/or identify the HPV66 genotype,
25) an oligonucleotide having the nucleotide sequence recited in SEQ ID nos. 98, 99, 100, 101, or 102 to detect and/or identify the HPV67 genotype,
26) an oligonucleotide having the nucleotide sequence recited in SEQ ID nos. 103, 104, 105, 131, or 132 to detect and/or identify the HPV68 genotype,
27) an oligonucleotide having the nucleotide sequence recited in SEQ ID nos. 106, 107, 108, or 133 to detect and/or identify the HPV70 genotype,
28) an oligonucleotide having the nucleotide sequence recited in SEQ ID nos. 109, 110, 111, 112, or 134 to detect and/or identify the HPV73 genotype, and
29) an oligonucleotide having the nucleotide sequence recited in SEQ ID nos. 113, 114, 115, 116, or 135 to detect and/or identify the HPV82 genotype.

A more preferred embodiment relates to providing an oligonucleotide that can be used as a probe for detecting and/or identifying genital HPV genotypes and that is selected from the oligonucleotides having one of the nucleotide sequences recited in SEQ ID no. 19, SEQ ID no. 32, SEQ ID no. 41, SEQ ID no. 44, SEQ ID no. 48, SEQ ID no. 82, or SEQ ID no. 117 to SEQ ID no. 135.

The oligonucleotides of the invention, in particular those having the nucleotide sequences recited in SEQ ID nos. 1 to 7, advantageously permit the extremely specific amplification of nucleic acid areas in a large number of different human HPV types, and the invention in particular provides for the amplification of a specific area of HPV gene E1. Using the E1 gene as the target area for amplification and thus for detecting HPV types offers a number of substantial advantages over using other areas of the HPV genome.

The ring-shaped HPV genome, whose size is approximately 7.9 kB, consists of the genes E6, E7, E1, E2, E4, E5, L2, L1, and the "long control region" (LCR), and the genes are arranged on the genome in this sequence. When HPV infections occur, the virus is frequently integrated into the human genome, with parts of the virus genome often being deleted in the process. It is known, therefore, that in carcinomas, for example, the genes E2, E4, E5, and L2 may be at least partially deleted. Therefore, the genes E2, E4, E5, and L2 cannot be used as a target region for amplification, since it is not possible to reliably detect HPV-DNA in a sample. However, it is known that E1 very frequently remains intact when the virus is integrated into the human genome, and that, at the very least, E1 is deleted much less frequently than the L1 gene. Whether or not E1 always remains intact has not yet been determined with certainty. However, it is highly probable that E1 is also amplified when the virus is integrated into the human genome and that it can therefore be detected with a large number of HPV infections. Thus, when the oligonucleotide primers of the invention are used, it is possible in particular to detect persistent HPV infections in which the risk that cancer will develop is very large.

Even though the LCR region and the genes E6 and E7 also remain intact when the virus is integrated into the human genome and are not deleted, these genome regions are not suitable for use as target regions for the amplification of HPV-DNA because the sequences of these regions in some cases can diverge greatly among the various HPV types. The use of these genome regions as a target region for amplification would necessitate a multitude of different primer pairs in order to detect all HPV types. It is also known that the sequence of the L1 gene is not preserved as well with the individual HPV types as the sequences of other HPV genome regions, so that it is not possible to detect all HPV types. By contrast, the E1 gene has the advantage that it is preserved relatively well with the various HPV types, so that an extremely broad spectrum of the various HPV types is detected when the E1 gene is amplified. Minimal sequence differences between individual HPV types are compensated for in the invention: in a preferred embodiment of the invention, an equimolar mixture of various oligonucleotides, in particular of the oligonucleotides having the nucleotide sequences recited in SEQ ID nos. 2 to 6, is used as the forward primer so that an amplification product is obtained for all HPV types with a single amplification reaction and so that it is therefore possible to detect all HPV types.

By means of the invention the amplification product that is obtained using the forward and reverse primers of the invention is then detected using the oligonucleotide probes of the invention. The oligonucleotides that are used as probes in the invention permit individual HPV types to be systematically detected in an extremely advantageous manner and therefore permit the HPV types that are present in a biological sample to be typed. When the oligonucleotide probes of the invention are used, more than 20 genitally pathogenic HPV types that occur with great frequency can be detected and differentiated. In a more preferred embodiment of the invention the oligonucleotide probes of the invention are contained on a nucleotide array, so that a multitude of amplification products can be simply and easily tested in a short time and so that the HPV genotypes can be typed. The oligonucleotides of the invention therefore permit the extremely fast and efficient typing of papilloma viruses, while by contrast the typing methods that are known in the prior art require time- and cost-intensive sequence analyses or gel electrophoreses.

In particular, the invention permits the oligonucleotides of the invention and the processes of the invention for amplifying or detecting and typing human papilloma viruses that are performed using these oligonucleotides to be used in particular in cases in which an HPV infection has already been detected and has proved to be present. Thus, it is not intended that the oligonucleotides and processes of the invention be used primarily for screening HPV infections, but rather for typing such infections, in other words to detect and identify individual HPV genotypes. A conventional test, such as the Digene Hybrid Capture Test, can be used to identify or detect the HPV infection. The Hybrid Capture Test can be used to differentiate low-risk and high-risk types. Since this test is very often used to study high-risk types, it can be expected that the clinically relevant high-risk types will be the types that are primarily detected using this test, and that they can then be typed using the oligonucleotides of the invention or the processes of the invention.

In the context of the present invention, an "oligonucleotide" is understood to mean an isolated and purified molecule comprising from two to less than 100 nucleotides. The oligonucleotides of the invention may preferably be purified and isolated DNA, RNA, PNA, or LNA molecules or hybrid forms of such molecules.

"PNA" ("peptide nucleic acid" or "polyamide nucleic acid") sequences are molecules that are not negatively charged and that function in the same manner as DNA (Nielsen et al., Science, 254 (1991), 1497-1500; Nielsen et al., Biochemistry, 26 (1997), 5072-5077; Weiler et al., Nuc. Acids Res., (1997), 2792-2799). PNA sequences comprise a polyamide primary structure of N-(2-aminoethyl) glycine units, and they do not have any glucose units or phosphate groups. The various bases are attached to the primary structure by means of methylene-carbonyl bonds. "LNA" (locked nucleic acid) molecules are distinguished by the fact that their furanose ring confirmation is restricted by a methylene linker that connects the 2'-O position to the 4'-C position. LNAs are incorporated as individual nucleotides in nucleic acids, for example DNA or RNA. Like PNA molecules, LNA oligonucleotides are subject to the Watson-Crick base pairing rules, and they hybridize on complementary oligonucleotides. Compared with similar duplex molecules that are formed exclusively from DNA or RNA, LNA/DNA or LNA/RNA duplex molecules exhibit increased thermal stability.

In the invention, the oligonucleotides of the invention have nucleotide sequences that are partially or completely complementary to sequences from the E1 gene region of genital HPV genotypes. One particular element of the invention is that the oligonucleotides having the nucleotide sequences recited in SEQ ID nos. 1 to 7 are complementary to consensus sequences that are present in the E1 gene region of at least 29 genital HPV genotypes, so that when these oligonucleotides are used as forward and/or reverse primers, it is possible to amplify the E1 gene region of all of these 29 genital HPV genotypes. At the same time, a further element of the invention is that the oligonucleotides having the nucleotide sequences recited in SEQ ID nos. 8 to 135, in particular the oligonucleotides having the sequences recited in SEQ ID nos. 19, 32, 41, 44, 48, 82, and 117 to 135, are only complementary in each case to sequences of a particular genital HPV genotype, however they do not exhibit any complementarity to the sequences of other genital HPV genotypes, so that the use of one of the nucleotides having the nucleotide sequences recited in SEQ ID nos. 8 to 135, in particular one of the oligonucleotides having the sequences recited in SEQ ID nos. 19, 32, 41, 44, 48, 82, and 117 to 135, permit the specific detection of a particular genital HPV genotype. In the context of the present invention, a nucleic acid is understood to be "complementary" to another nucleic acid if it is able to form a double strand with this other nucleic acid along its entire length or at least along the greatest part of its length, and if all of the nucleotides in this double strand are paired with each other by means of hydrogen bonds in accordance with the rules set forth by Watson and Crick.

In a further preferred embodiment of the invention, the oligonucleotides of the invention have a nucleotide sequence that is mutated relative to one of the nucleotide sequences recited in SEQ ID nos. 1 to 135, in particular relative to one of the nucleotide sequences recited in SEQ ID nos. 1 to 7, 19, 32, 41, 44, 48, 82, or 117 to 135, whereby the oligonucleotides are obtained through the:

a) deletion of 1 to 10 nucleotides in one of the nucleotide sequences recited in SEQ ID nos. 1 to 135, in particular in one of the nucleotide sequences recited in SEQ ID nos. 1 to 7, 19, 32, 41, 44, 48, 82, or 117 to 135, b) addition of 1 to 10 nucleotides in one of the nucleotide sequences recited in SEQ ID nos. 1 to 135, in particular in one of the nucleotide sequences recited in SEQ ID nos. 1 to 7, 19, 32, 41, 44, 48, 82, or 117 to 135, and/or c) substitution of 1 to 3 nucleotides in one of the nucleotide sequences recited in SEQ ID nos. 1 to 135, in particular in one of the nucleotide sequences recited in SEQ ID nos. 1 to 7, 19, 32, 41, 44, 48, 82, or 117 to 135.

In accordance with the invention, the deletion or addition of the nucleotides is present at the 5' end and/or 3' end of one of the nucleotide sequences recited in SEQ ID nos. 1 to 135. In the case of an addition, it is also preferred that the additional nucleotides, together with one of the nucleotide sequences recited in SEQ ID nos. 1 to 135, form a sequence that is complementary to the corresponding target sequences in the E1 gene region along its entire length or at least along the greatest part of its length.

Of course, the present invention also comprises oligonucleotides that have a nucleotide sequence that is complementary along its entire length to one of the nucleotide sequences recited in SEQ ID nos. 1 to 135, in particular to one of the nucleotide sequences recited in SEQ ID nos. 1 to 7, 19, 32, 41, 44, 48, 82, or 117 to 135, or to one of the nucleotide sequences that is mutated in accordance with the invention that are characterized by the fact that they exhibit an addition and/or deletion of 1 to 10 nucleotides, and/or a substitution of 1 to 3 nucleotides relative to the nucleotide sequences recited in SEQ ID nos. 1 to 135, in particular one of the nucleotide sequences recited in SEQ ID nos. 1 to 7, 19, 32, 41, 44, 48, 82, or 117 to 135.

The present invention also solves the underlying technical problem by providing a primer pair to amplify a nucleic acid region of a genital human papilloma virus comprising a forward primer and a reverse primer, wherein the forward primer is selected from the group comprising:

a) an oligonucleotide having one of the nucleotide sequences recited in SEQ ID nos. 1 to 6, b) an oligonucleotide which, compared with the oligonucleotide of a), has a mutated nucleotide sequence, in other words with the addition and/or substitution of 1 to 10 nucleotides and/or a substitution of 1 to 3 nucleotides, and c) a mixture of the oligonucleotides of a) and/or b), and the reverse primer is selected from the group comprising:

d) an oligonucleotide having the nucleotide sequence recited in SEQ ID no. 7, e) an oligonucleotide that has a nucleotide sequence that is mutated relative to the oligonucleotide of d), in other words with an addition and/or deletion of 1 to 10 nucleotides and/or a substitution of 1 to 3 nucleotides, and f) a mixture of the oligonucleotides of d) and e).

In a preferred embodiment the primer pair comprises an equimolar mixture of the oligonucleotides having the nucleotide sequences recited in SEQ ID nos. 2 to 6 as the forward primer, and the oligonucleotide having the nucleotide sequence recited in SEQ ID no. 7 as the reverse primer.

In an additional preferred embodiment of the invention, oligonucleotides having one of the nucleotide sequences recited in SEQ ID nos. 8 to 135, in particular of one of the nucleotide sequences recited in SEQ ID nos. 19, 32, 41, 44, 48, 82, or 117 to 135, of a mutated nucleotide sequence thereof, or of a complementary sequence thereof can be part of a longer oligonucleotide or polynucleotide. The longer oligonucleotide or polynucleotide, which is also referred to below as a nucleic acid molecule, therefore also comprises additional nucleotides and/or nucleotide sequences in addition to one of the nucleotide sequences recited in SEQ ID nos. 8 to 135, in particular one of the nucleotide sequences recited in SEQ ID nos. 19, 32, 41, 44, 48, 82, or 117 to 135, a mutated sequence thereof, or a complementary sequence. In the context of the present invention, a "polynucleotide" is understood to mean a purified and isolated molecule that consists of at least one hundred nucleotides.

The present invention therefore also relates to a preferably purified and isolated nucleic acid molecule comprising at least one region that has one of the nucleotide sequences recited in SEQ ID nos. 8 to 135, in particular one of the nucleotide sequences recited in SEQ ID nos. 1 to 7, 19, 32, 41, 44, 48, 82, or 117 to 135, a mutated nucleotide sequence thereof, obtained by the deletion and/or addition of 1 to 10 nucleotides and/or substitution of 1 to 3 nucleotides of one of the nucleotide sequences recited in SEQ ID nos. 8 to 135, in particular one of the nucleotide sequences recited in SEQ ID nos. 1 to 7, 19, 32, 41, 44, 48, 82, or 117 to 135, or a nucleotide sequence that is complementary to these sequences, and one or more additional regions having a total length of at least one nucleotide. The nucleic acid molecule of the invention may be a relatively long oligonucleotide or a polynucleotide. If the nucleic acid molecule of the invention is present as a relatively long oligonucleotide, the total length of the relatively long oligonucleotide of the invention is no more than 99 nucleotides. If the relatively long oligonucleotide of the invention comprises, for example, one of the nucleotide sequences recited in SEQ ID nos. 8 to 135, the additional regions therefore may have a total length from at least 1 nucleotide to a maximum of 69 to 72 nucleotides. If the relatively long oligonucleotide of the invention comprises a nucleotide sequence that is mutated relative to one of the nucleotide sequences recited in SEQ ID nos. 8 to 135 by means of the addition of 1 to 10 nucleotides, the additional regions may have a total length from at least 1 nucleotide to a maximum of 68-71 nucleotides (in the case of the addition of a nucleotide) and 59-62 nucleotides (in the case of the addition of 10 nucleotides), respectively. The total length of the additional regions of the nucleic acid molecule that is present as a relatively long oligonucleotide is preferably from 1 to about 60, more preferably from 1 to about 50, even more preferably from 1 to about 40, and most preferably from 1 to about 30 nucleotides. If the nucleic acid molecule of the invention is present as a polynucleotide, its total length is at least 100 nucleotides. The total length of the additional regions of the polynucleotide of the invention ranges from at least approximately 70 to 80 nucleotides to about 1000 nucleotides, preferably about 70-80 nucleotides to about 500 nucleotides, more preferably about 70-80 nucleotides to about 250 nucleotides, and most preferably about 70-80 nucleotides to about 100 nucleotides, depending on whether the polynucleotide of the invention comprises one of the sequences recited in SEQ ID nos. 8 to 135, or a mutated sequence thereof.

The region of which at least one is contained in the nucleic acid molecule of the invention and that has one of the nucleotide sequences recited in SEQ ID nos. 8 to 135, in particular one of the nucleic acid sequences recited in SEQ ID nos. 1 to 7, 19, 32, 41, 44, 48, 82, or 117 to 135, a mutated nucleotide sequence thereof, or a complementary nucleotide sequence thereof, may be located at the 5' end and/or at the 3' end of the sequence of the nucleic acid molecule and/or between the additional regions.

In a preferred embodiment of the invention these additional areas of the nucleic acid molecule of the invention have nucleotide sequences that are complementary to the sequences of an amplification product that may be obtained by means of an amplification process using a nucleic acid region of a genital human papilloma virus as the template and of a primer pair of the invention. For example, the additional regions may comprise multiple repetitions of the region that has one of the nucleotide sequences recited in SEQ ID nos. 8 to 135, a mutated nucleotide sequence thereof, or a complementary nucleotide sequence thereof. In the invention it is possible for the repetitions of this region to be separated in each case by spacers having a length of at least a nucleotide or at least a phosphate or at least a carbon atom, or at least an amino group.

In a further preferred embodiment of the invention the additional regions of the nucleic acid molecules of the invention have nucleotide sequences that are not complementary to the sequences of an amplification product that is obtained by means of an amplification process using a nucleic acid region of a genital human papilloma virus as the template and using a primer pair of the invention, and therefore do not hybridize with the amplification product. For example, the additional regions of the nucleic acid molecules of the invention may have poly-A or poly-T nucleotide sequences.

The present invention also relates to nucleic acid molecules that have a nucleotide sequence that is complementary along its entire length to the nucleotide sequence of a nucleic acid molecule of the invention. In the invention, the nucleic acid molecules of the invention are present as preferably purified and isolated DNA molecules, RNA molecules, PNA molecules, LNA molecules, or hybrid forms thereof.

The present invention also solves the underlying technical problem by providing a process for amplifying a region of a nucleic acid of a genital human papilloma virus that is present in a biological sample, comprising the implementation of a nucleic acid amplification process using a primer pair comprising a forward primer and a reverse primer, wherein the forward primer is selected from the group comprising:

a) an oligonucleotide having a nucleotide sequence recited in SEQ ID nos. 1 to 6, b) an oligonucleotide that has a nucleotide sequence that is mutated relative to the oligonucleotide of a), and c) a mixture of the oligonucleotides of a) and/or b), and the reverse primer is selected from the group comprising:

d) an oligonucleotide having the nucleotide sequence set forth in SEQ ID no. 7, e) an oligonucleotide that has a nucleotide sequence that is mutated relative to the oligonucleotide of d), and f) a mixture of the oligonucleotides of d) and e).

By using the process of the invention it is possible to advantageously amplify specific nucleic acid regions, in particular a region of the preserved E1 gene, of a multitude of genital human papilloma viruses. The amplification products that are obtained through this process allow one to detect the presence of a papilloma virus or of a number of papilloma viruses in a biological sample, while the absence of an amplification product indicates that no HPV virus is present in the sample being tested. The amplification product obtained using the amplification process of the invention may be used with the aid of the oligonucleotide and/or polynucleotide probes of the invention to type the detected papilloma virus or the detected papilloma viruses.

In the context of the present invention, the term "biological sample" means a skin or mucous membrane smear, an organ biopsy, a tissue biopsy, a body fluid, or a body secretion. The sample may be taken from a living or dead organism, organ, or tissue. In the context of the invention a "biological sample" may also be a culture or culture medium, for example a medium in which human or animal cells were cultivated. A sample as defined in the invention may also be an aqueous solution, emulsion, dispersion, or suspension that contains isolated and purified human papilloma viruses or components thereof. A biological sample may have already been subjected to purification steps, but it may also be present in an unpurified form.

In a preferred embodiment of the invention the biological sample is a smear from the cervix, a fresh cervix tissue sample, a fixed cervix tissue sample, or a cross-sectional specimen of a cervix tissue sample. In the invention the sample may in particular be a sample that is taken as part of cytological testing and/or of a colposcopy in order to identify epithelial changes associated with HPV of the subclinical or clinically manifest stage of an HPV infection.

In the invention the nucleic acid that is to be amplified may be purified and/or isolated from the biological sample before the primer of the invention is used. The purification and isolation of the nucleic acid that is to be amplified—in other words, the HPV-DNA that is to be amplified—may be performed using methods that are known in the prior art.

In a preferred embodiment of the invention, a PCR (polymerase chain reaction) process is used to amplify the nucleic acid. The PCR process is a process that is used to systematically multiply a specific nucleic acid or a region thereof in a mixture of different or similar sequences. The process is based on the principle of repeatedly using certain reaction steps, namely the denaturing of a double-strand nucleic acid molecule that is to be amplified, the positioning of primers on the resulting single-strand nucleic acid molecules (annealing) and a synthesis of complementary strands beginning at the annealed primers (extension), whereby the single-strand nucleic acid molecules that serve as templates are obtained. In a first step, therefore, the double-strand nucleic acid that is to be amplified is denatured at a suitable temperature, whereby single-strand nucleic acids are obtained as templates. This is followed by a lowering of the temperature during which oligonucleotides (primers) that are present in excess amounts in the reaction mixture and whose sequences are complementary to the beginning or end of the nucleic acids that are to be amplified hybridize with the complementary nucleic acid regions. At a temperature that can correspond to the hybridization temperature of approximately 50° C. to 72° C., but that can also be set to the optimal temperature of 72° C. to 75° C. for the preferably thermostable DNA polymerase, the polymerase then synthesizes copies of the initial nucleic acid beginning at the primers in the form of primer extension products, whereby the length of the copies is determined by the distance between the primers. This leads to a chain reaction obtained by performing a cycle comprising the denaturing of the primer extension product of the template, the treatment of the resulting single-strand molecules with the same primers, and the formation of additional primer extension products. The cycle is repeated until the target nucleic acid that is to be amplified is present in the desired amount.

In a preferred embodiment of the invention the PCR amplification of the HPV-DNA that is to be detected is performed under the following temperature conditions:
a) Heat to 95° C., increasing the temperature by 1° C. per second,
b) Hold the temperature at 95° C. for 10 minutes,
c) Perform 40 cycles, each comprising 30 seconds at 95° C., 30 seconds at 55° C., and one minute at 72° C.,
d) Hold the temperature at 72° C. for five minutes, and
e) Cool to 4° C.

In the invention the oligonucleotides that are used as forward primers and reverse primers are used in the nucleic acid amplification reaction at a concentration of 0.5-1 pmoles/µL. An equimolar mixture of the oligonucleotides having the nucleotide sequences recited in SEQ ID nos. 2 to 6 is especially preferred as the forward primer, and each oligonucleotide is present at a concentration of 0.1-0.2 pmoles/µL; and the oligonucleotide having the nucleotide sequence recited in SEQ ID no. 7 is used at a concentration of 0.5-1 pmoles/µL as the reverse primer. The oligonucleotides that are used as the forward and reverse primers may be used as DNA, RNA, PNA, or LNA molecules or hybrid forms thereof.

In a different embodiment of the invention, the nucleic acid amplification process is an LCR (ligase chain reaction), an NASBA process, or an isothermal process. The LCR process is based on repeatedly performing two reaction steps. In the first step a double-strand nucleic acid is denatured at high temperature. In the second step two sets of adjacent complementary oligonucleotides are hybridized onto the single-strand nucleic acid obtained in the first step and are ligated with each other. The products of the ligation from this reaction are used as templates to repeat the process. Like the PCR process, the LCR process results in an exponential amplification of the ligation products.

In the invention a specific region of the HPV gene E1 is amplified in the amplification process of the invention. Of course, the invention also provides that the amplified nucleic acid region may then be purified and/or isolated in order, for example, to conduct HPV typing.

In the invention the amplification product that is prepared using the process of the invention may be provided with a marking during or after the amplification to permit the subsequent detection of the amplification process, in particular using one or more of the oligonucleotides of the invention that are used in accordance with the invention as probes and that have the nucleotide sequences recited in SEQ ID nos. 8 to 135, preferably with the nucleotide sequences recited in SEQ ID nos. 1 to 7, 19, 32, 41, 44, 48, 82, or 117 to 135, mutated nucleotide sequences thereof, or complementary nucleotide sequences thereof, and/or of the nucleic acid molecules of the invention. Marking of the amplification product during the amplification reaction may be accomplished, for example, using marked primers and/or marked nucleotides. Of course, the amplification product may [be marked] using prior-art methods after the completion of the amplification reaction. In the invention, the amplification product may be marked for example using fluorescent dyes, biotin, haptenes, antigens, chemical groups, for example by using aminoallyl-marked nucleotides, or by using a succinimide reaction to attach a marker to the aminoallyl-marked nucleotide, radioactive substances, enzymatic markers, etc. The detection of a marked amplification product may be accomplished, for example, using fluorescence methods, chemoluminescence methods, densitometry methods, photometry methods, precipitation reactions, enzymatic reactions including enzymatic reinforcement reactions, SPR ("surface plamon resonance") methods, ellipsometry methods, measurement of the index of refraction, measurement of reflectance, and similar methods.

The present invention also solves the underlying technical problem by providing a process for detecting and/or identifying an individual genital HPV genotype, comprising the testing of a nucleic acid of the HPV gene E1 or a portion thereof present in a biological sample, by hybridizing with at least one probe, whereby the probe is selected from the group comprising:
a) HPV genotype-specific oligonucleotides having the nucleotide sequences recited in SEQ ID nos. 8 to 135, preferably the nucleotide sequences recited in SEQ ID nos. 1 to 7, 19, 32, 41, 44, 48, 82, or 117 to 135,
b) oligonucleotides that have a nucleotide sequence that is mutated relative to one of the oligonucleotides of a),
c) oligonucleotides that have a nucleotide sequence that is complementary to one of the oligonucleotides of a) or b),
d) nucleic acid molecules comprising at least one region of the nucleotide sequences recited in SEQ ID nos. 8 to 135, in particular one of the nucleotide sequences recited in SEQ ID nos. 1 to 7, 19, 32, 41, 44, 48, 82, or 117 to 135, a mutated nucleotide sequence thereof, or a complementary nucleotide sequence thereof, and
e) mixtures of the oligonucleotides of a) to c) and/or the nucleic acid molecules of d),
and the detection of the hybridization.

The process of the invention to detect and/or identify an individual genital HPV genotype is used in particular to type HPV genotypes whose presence in a biological sample was determined to be assured by means of a different process. The detection of the presence of an HPV infection may be carried out, for example, using the HCM method, which can be used to distinguish between high-risk types and low-risk types.

In a preferred embodiment of the process of the invention, the HPV nucleic acid that is present in the biological sample is amplified prior to hybridization with the oligonucleotide or nucleic acid molecule probe(s), and an amplification product that can be tested in the process of the invention to carry out typing by means of the oligonucleotide and/or nucleic acid molecule probes of the invention was obtained. The amplification of the HPV nucleic acid using the process of the invention for amplifying HPV nucleic acids, in other words using the oligonucleotides having the nucleotide sequences recited in SEQ ID nos. 1, 2, 3, 4, 5, and 6 as the forward primer, and using the oligonucleotide having the nucleotide sequence recited in SEQ ID no. 7 as the reverse primer, is especially preferred. In the invention the biological sample that is to be subjected to typing in accordance with the invention comprises an amplified nucleic acid region obtained by means of the nucleic acid amplification process of the invention.

Of course, the process of the invention for detecting and/or identifying, in other words for typing, a genital HPV genotype can also be performed on a biological sample in which an HPV nucleic acid region was not amplified. In a further embodiment of the invention the biological sample is a smear specimen from the cervix, a fresh cervix tissue sample, a fixed cervix tissue sample, or a cross-sectional specimen of such a tissue sample.

The hybridization with the oligonucleotide or nucleic acid molecule probes of the invention is performed under conditions that are described in the prior art.

In the invention a hybridization with an oligonucleotide having the nucleotide sequence recited in SEQ ID nos. 8, 9, or 117, preferably having the nucleotide sequence recited in SEQ ID no. 117, with a mutated nucleotide sequence thereof, or with a complementary nucleotide sequence thereof, or with a nucleic acid molecule that comprises one of the nucleotide sequences recited in SEQ ID nos. 8, 9, or 117, preferably the nucleotide sequence recited in SEQ ID no. 117, a mutated nucleotide sequence thereof, or a complementary nucleotide sequence indicates the HPV6 genotype, preferably the HPV6b genotype.

A hybridization with an oligonucleotide having the nucleotide sequence recited in SEQ ID nos. 10, 11, 12, 13, 14, 15, 16, 17, or 118, preferably the nucleotide sequence recited in SEQ ID no. 118, a mutated nucleotide sequence thereof, or a complementary nucleotide sequence thereof, or with a nucleic acid molecule that comprises one of the nucleotide sequences recited in SEQ ID nos. 10, 11, 12, 13, 14, 15, 16, 17, or 118, preferably the nucleotide sequence recited in SEQ ID no. 118, a mutated nucleotide sequence thereof, or a complementary nucleotide sequence thereof, indicates in the invention the HPV11 genotype.

In the invention, a hybridization with an oligonucleotide having the nucleotide sequence recited in SEQ ID nos. 18, 19, or 20, preferably the nucleotide sequence recited in SEQ ID no. 19, with a mutated nucleotide sequence thereof, or with a complementary nucleotide sequence thereof, or with a nucleic acid molecule that comprises one of the nucleotide sequences recited in SEQ ID nos. 18, 19, or 20, preferably the nucleotide sequence set forth in SEQ ID no. 19, a mutated nucleotide sequence thereof, or a complementary nucleotide sequence thereof, indicates the HPV16 genotype.

In the invention a hybridization with an oligonucleotide having the nucleotide sequence recited in SEQ ID nos. 21, 22, 23, 24, or 119, preferably the nucleotide sequence recited in SEQ ID no. 119, a mutated nucleotide sequence thereof, or a complementary nucleotide sequence thereof, or with a nucleic acid molecule that comprises one of the nucleotide sequences recited in SEQ ID nos. 21, 22, 23, 24, or 119, preferably the nucleotide sequence recited in SEQ ID no. 119, a mutated nucleotide sequence thereof, or a complementary nucleotide sequence thereof, indicates the HPV18 genotype.

Moreover, in the invention a hybridization with an oligonucleotide having the nucleotide sequence recited in SEQ ID nos. 25, 26, 27, or 28, a mutated nucleotide sequence thereof, or a complementary nucleotide sequence thereof, or with a nucleic acid molecule that comprises one of the nucleotide sequences recited in SEQ ID nos. 25, 26, 27, or 28, a mutated nucleotide sequence thereof, or a complementary nucleotide sequence thereof, indicates the HPV26 genotype.

A hybridization with an oligonucleotide having the nucleotide sequence recited in SEQ ID nos. 29, 30, 31, or 120, preferably the nucleotide sequence recited in SEQ ID no. 120, a mutated nucleotide sequence thereof, or a complementary nucleotide sequence thereof, or with a nucleic acid molecule comprising one of the nucleotide sequences recited in SEQ ID nos. 29, 30, 31, or 120, preferably the nucleotide sequence recited in SEQ ID no. 120, a mutated nucleotide sequence thereof, or a complementary nucleotide sequence thereof, indicates in the invention the HPV31 genotype.

Moreover, in the invention a hybridization with an oligonucleotide having the nucleotide sequence recited in SEQ ID nos. 32, 33, or 34, preferably the nucleotide sequence recited in SEQ ID no. 32, a mutated nucleotide sequence thereof, or a complementary nucleotide sequence thereof, or with a nucleic acid molecule that comprises one of the nucleotide sequences recited in SEQ ID nos. 32, 33, or 34, preferably the nucleotide sequence recited in SEQ ID no. 32, a mutated nucleotide sequence thereof, or a complementary nucleotide sequence thereof, indicates the HPV 33 genotype.

In a further embodiment of the invention, a hybridization with an oligonucleotide having the nucleotide sequence recited in SEQ ID nos. 35, 36, 37, 38, or 39, a mutated nucleotide sequence thereof, or a complementary nucleotide sequence thereof, or with a nucleic acid molecule comprising one of the nucleotide sequences recited in SEQ ID nos. 35, 36, 37, 38, or 39, a mutated nucleotide sequence thereof, or a complementary nucleotide sequence thereof, indicates the HPV34 genotype.

In the invention a hybridization with an oligonucleotide having the nucleotide sequence recited in SEQ ID nos. 40 or 41, preferably the nucleotide sequence recited in SEQ ID no. 41, a mutated nucleotide sequence thereof, or a complementary nucleotide sequence thereof, or with a nucleic acid molecule that comprises one of the nucleotide sequences recited in SEQ ID nos. 40 or 41, preferably the nucleotide sequence recited in SEQ ID no. 41, a mutated nucleotide sequence thereof, or a complementary nucleotide sequence thereof, indicates the HPV35 genotype, preferably the HPV35h genotype.

In the invention a hybridization with an oligonucleotide having the nucleotide sequence recited in SEQ ID nos. 42, 43, 44, 45, or 46, preferably the nucleotide sequence recited in SEQ ID no. 44, a mutated nucleotide sequence thereof, or a complementary nucleotide sequence thereof, or with a nucleic acid molecule that comprises one of the nucleotide sequences recited in SEQ ID nos. 42, 43, 44, 45, or 46, preferably the nucleotide sequence recited in SEQ ID no. 44, a mutated nucleotide sequence thereof, or a complementary nucleotide sequence thereof, indicates the HPV39 genotype.

A hybridization with an oligonucleotide having the nucleotide sequence recited in SEQ ID nos. 47, 48, 49, or 50, preferably the nucleotide sequence recited in SEQ ID no. 48, a mutated nucleotide sequence thereof, or a complementary nucleotide sequence thereof, or with a nucleic acid molecule that comprises one of the nucleotide sequences recited in SEQ ID nos. 47, 48, 49, or 50, preferably the nucleotide sequence recited in SEQ ID no. 48, a mutated nucleotide sequence thereof, or a complementary nucleotide sequence thereof, indicates the HPV40 genotype in the invention.

In the invention, moreover, a hybridization with an oligonucleotide having the nucleotide sequence recited in SEQ ID nos. 51, 52, or 121, preferably the nucleotide sequence recited in SEQ ID no. 121, a mutated nucleotide sequence thereof, or a complementary nucleotide sequence thereof, or with a nucleic acid molecule that comprises one of the nucleotide sequences recited in SEQ ID nos. 51, 52, or 121, preferably the nucleotide sequence recited in SEQ ID no. 121, a mutated nucleotide sequence thereof, or a complementary nucleotide sequence thereof, indicates the HPV42 genotype.

In the invention, moreover, a hybridization with an oligonucleotide having the nucleotide sequence recited in SEQ ID no. 122, a mutated nucleotide sequence thereof, or a complementary nucleotide sequence thereof, or with a nucleic acid molecule that comprises one of the nucleotide sequences recited in SEQ ID no. 122, a mutated nucleotide sequence thereof, or a complementary nucleotide sequence thereof, indicates the HPV43 genotype.

A hybridization with an oligonucleotide having the nucleotide sequence recited in SEQ ID nos. 53, 54, 55, or 123, preferably the nucleotide sequence recited in SEQ ID no. 123, a mutated nucleotide sequence thereof, or a complementary nucleotide sequence thereof, or with a nucleic acid molecule that comprises one of the nucleotide sequences recited in SEQ ID nos. 53, 54, 55, or 123, preferably the nucleotide sequence recited in SEQ ID no. 123, a mutated nucleotide sequence thereof, or a complementary nucleotide sequence thereof, indicates the HPV44 genotype in the invention.

In the invention, moreover, a hybridization with an oligonucleotide having the nucleotide sequence recited in SEQ ID nos. 56, 57, 58, 59, 60, 61, or 124, preferably the nucleotide sequence recited in SEQ ID no. 124, a mutated nucleotide sequence thereof, or a complementary nucleotide sequence thereof, or with a nucleic acid molecule that comprises one of the nucleotide sequences recited in SEQ ID nos. 56, 57, 58, 59, 60, 61, or 124, preferably the nucleotide sequence recited in SEQ ID no. 124, a mutated nucleotide sequence thereof, or a complementary nucleotide sequence thereof, indicates the HPV45 genotype.

A hybridization with an oligonucleotide having the nucleotide sequence recited in SEQ ID nos. 62, 63, 64, or 125, preferably the nucleotide sequence recited in SEQ ID no. 125, a mutated nucleotide sequence thereof, or a complementary nucleotide sequence thereof, or with a nucleic acid molecule that comprises one of the nucleotide sequences recited in SEQ ID nos. 62, 63, 64, or 125, preferably the nucleotide sequence recited in SEQ ID no. 125, a mutated nucleotide sequence thereof, or a complementary nucleotide sequence thereof, indicates the HPV51 genotype in the invention.

In the invention, moreover, a hybridization with an oligonucleotide having the nucleotide sequence recited in SEQ ID nos. 65, 66, 67, or 126, preferably the nucleotide sequence recited in SEQ ID no. 126, a mutated nucleotide sequence thereof, or a complementary nucleotide sequence thereof, or with a nucleic acid molecule that comprises one of the nucleotide sequences recited in SEQ ID nos. 65, 66, 67, or 126, preferably the nucleotide sequence recited in SEQ ID no. 126, a mutated nucleotide sequence thereof, or a complementary nucleotide sequence thereof, indicates the HPV52 genotype.

A hybridization with an oligonucleotide having the nucleotide sequence recited in SEQ ID nos. 68, 69, 70, 71, 72, 73, or 127, preferably the nucleotide sequence recited in SEQ ID no. 127, a mutated nucleotide sequence thereof, or a complementary nucleotide sequence thereof, or with a nucleic acid molecule that comprises one of the nucleotide sequences recited in SEQ ID nos. 68, 69, 70, 71, 72, 73, or 127, preferably the nucleotide sequence recited in SEQ ID no. 127, a mutated nucleotide sequence thereof, or a complementary nucleotide sequence thereof, indicates the HPV53 genotype in the invention.

In a further embodiment of the process of the invention, a hybridization with an oligonucleotide having the nucleotide sequence recited in SEQ ID nos. 74, 75, 76, or 77, a mutated nucleotide sequence thereof, or a complementary nucleotide sequence thereof, or with a nucleic acid molecule that comprises one of the nucleotide sequences recited in SEQ ID nos. 74, 75, 76, or 77, a mutated nucleotide sequence thereof, or a complementary nucleotide sequence thereof, indicates the HPV54 genotype.

A hybridization with an oligonucleotide having the nucleotide sequence recited in SEQ ID nos. 78, 79, 80, 81, or 128, preferably the nucleotide sequence recited in SEQ ID no. 128, a mutated nucleotide sequence thereof, or a complementary nucleotide sequence thereof, or with a nucleic acid molecule that comprises one of the nucleotide sequences recited in SEQ ID nos. 78, 79, 80, 81, or 128, preferably the nucleotide sequence recited in SEQ ID no. 128, a mutated nucleotide sequence thereof, or a complementary nucleotide sequence thereof, indicates the HPV56 genotype in the invention.

In the invention, moreover, a hybridization with an oligonucleotide having the nucleotide sequence recited in SEQ ID nos. 82, 83, 84, 85, or 86, preferably the nucleotide sequence recited in SEQ ID no. 82, a mutated nucleotide sequence thereof, or a complementary nucleotide sequence thereof, or with a nucleic acid molecule that comprises one of the nucleotide sequences recited in SEQ ID nos. 82, 83, 84, 85, or 86, preferably the nucleotide sequence recited in SEQ ID no. 82, a mutated nucleotide sequence thereof, or a complementary nucleotide sequence thereof, indicates the HPV58 genotype.

A hybridization with an oligonucleotide having the nucleotide sequence recited in SEQ ID nos. 87 or 129, preferably the nucleotide sequence recited in SEQ ID no. 129, a mutated nucleotide sequence thereof, or a complementary nucleotide sequence thereof, or with a nucleic acid molecule that comprises one of the nucleotide sequences recited in SEQ ID nos. 87 or 129, preferably the nucleotide sequence recited in SEQ ID no. 129, a mutated nucleotide sequence thereof, or a complementary nucleotide sequence thereof, indicates the HPV59 genotype in the invention.

In a further embodiment of the invention, a hybridization with an oligonucleotide having the nucleotide sequence recited in SEQ ID nos. 88, 89, 90, 91, 92, 93, or 94, a mutated nucleotide sequence thereof, or a complementary nucleotide sequence thereof, or with a nucleic acid molecule comprising one of the nucleotide sequences recited in SEQ ID nos. 88, 89, 90, 91, 92, 93, or 94, a mutated nucleotide sequence thereof, or a complementary nucleotide sequence thereof, indicates the HPV61 genotype.

A hybridization with an oligonucleotide having the nucleotide sequence recited in SEQ ID nos. 95, 96, 97, or 130, preferably the nucleotide sequence recited in SEQ ID no. 130, a mutated nucleotide sequence thereof, or a complementary nucleotide sequence thereof, or with a nucleic acid molecule that comprises one of the nucleotide sequences recited in SEQ ID nos. 95, 96, 97, or 130, preferably the nucleotide sequence recited in SEQ ID no. 130, a mutated nucleotide sequence thereof, or a complementary nucleotide sequence thereof, indicates the HPV66 genotype in the invention.

In the invention, moreover, a hybridization with an oligonucleotide having the nucleotide sequence recited in SEQ ID nos. 98, 99, 100, 101, or 102, a mutated nucleotide sequence thereof, or a complementary nucleotide sequence thereof, or with a nucleic acid molecule that comprises one of the nucleotide sequences recited in SEQ ID nos. 98, 99, 100, 101, or 102, a mutated nucleotide sequence thereof, or a complementary nucleotide sequence thereof, indicates the HPV67 genotype.

A hybridization with an oligonucleotide having the nucleotide sequence recited in SEQ ID nos. 103, 104, 105, 131, or 132, preferably the nucleotide sequence recited in SEQ ID no. 131 or 132, a mutated nucleotide sequence thereof, or a complementary nucleotide sequence thereof, or with a nucleic acid molecule that comprises one of the nucleotide sequences recited in SEQ ID nos. 103, 104, 105, 131, or 132, preferably the nucleotide sequence recited in SEQ ID no. 131 or 132, a mutated nucleotide sequence thereof, or a complementary nucleotide sequence thereof, indicates the HPV68 genotype in the invention.

In a further embodiment of the invention a hybridization with an oligonucleotide having the nucleotide sequence recited in SEQ ID nos. 106, 107 108, or 133, preferably the nucleotide sequence recited in SEQ ID no. 133, a mutated nucleotide sequence thereof, or a complementary nucleotide sequence thereof, or with a nucleic acid molecule that comprises one of the nucleotide sequences recited in SEQ ID nos. 106, 107 108, or 133, preferably the nucleotide sequence recited in SEQ ID no. 133, a mutated nucleotide sequence thereof, or a complementary nucleotide sequence thereof, indicates the HPV70 genotype.

A hybridization with an oligonucleotide having the nucleotide sequence recited in SEQ ID nos. 109, 110, 111, 112, or 134, preferably the nucleotide sequence recited in SEQ ID nos. 134, a mutated nucleotide sequence thereof, or a complementary nucleotide sequence thereof, or with a nucleic acid molecule that comprises one of the nucleotide sequences recited in SEQ ID nos. 109, 110, 111, 112, or 134, preferably the nucleotide sequence recited in SEQ ID no. 134, a mutated nucleotide sequence thereof, or a complementary nucleotide sequence thereof, indicates the HPV73 genotype in the invention.

A hybridization with an oligonucleotide having the nucleotide sequence recited in SEQ ID nos. 113, 114, 115, 116, or 135, preferably the nucleotide sequence recited in SEQ ID nos. 135, a mutated nucleotide sequence thereof, or a complementary nucleotide sequence thereof, or with a nucleic acid molecule that comprises one of the nucleotide sequences recited in SEQ ID nos. 113, 114, 115, 116, or 135, preferably the nucleotide sequence recited in SEQ ID no. 135, a mutated nucleotide sequence thereof, or a complementary nucleotide sequence thereof, indicates the HPV82 genotype in the invention.

The oligonucleotide or nucleic acid molecule that is used as the probe can be present as a DNA, RNA, PNA, or LNA molecule, or as a hybrid form.

The processes of the invention to amplify nucleic acid regions of human papilloma viruses and to detect and/or identify genital HPV genotypes may be used in particular for the diagnosis and/or early detection of diseases that are caused by genital human papilloma viruses. The processes of the invention may be used in a preferred embodiment as part of a process for the diagnosis and/or early detection of diseases, in particular cancer diseases, for example uterine cancer. The processes of the invention may also be used as part of an early-detection test to identify cancer diseases. The processes of the invention result in assured positive findings with respect to an HPV infection and can therefore be used as the starting point for systematic treatment.

The present invention also solves the underlying technical problem by providing a nucleotide array for detecting and/or identifying the genotype of a human papilloma virus contained in a biological sample, in particular by using the process of the invention to detect and/or identify the genotype of HPV viruses, comprising a solid carrier having one surface and at least one initial oligonucleotide or nucleic acid molecule that is attached to the surface of the carrier and that is suitable for use to detect and/or identify a genital HPV genotype selected from the group comprising:

a) HPV genotype-specific oligonucleotides having the nucleotide sequences recited in SEQ ID nos. 8 to 135, preferably the nucleotide sequences recited in SEQ ID nos. 19, 32, 41, 44, 48, 82, and 117 to 135, b) oligonucleotides that have a mutated nucleotide sequence relative to one of the oligonucleotides of a), c) oligonucleotides that have a nucleotide sequence that is complementary to one of the oligonucleotides of a) or b), d) nucleic acid molecules comprising a region that has one of the nucleotide sequences recited in SEQ ID nos. 8 to 135, preferably one of the nucleotide sequences recited in SEQ ID nos. 19, 32, 41, 44, 48, 82, and 117 to 135, a mutated nucleotide sequence thereof, or a complementary nucleotide sequence thereof, and e) mixtures of the oligonucleotides of a) to c) and/or the nucleic acid molecules of d).

In the context of the present invention a "nucleotide array" or a "nucleotide chip" is understood to mean a device that contains a plurality of various nucleic acid molecules or nucleotide sequences, for example DNA molecules, RNA molecules, PNA molecules, LNA molecules, and/or hybrid forms thereof, in an immobilized form, and with whose aid by means of nucleic acid hybridization a small amount of a complementary nucleic acid can be detected in a small sample liquid. Using the nucleotide array of the invention it is possible, on the one hand, to easily detect human papilloma viruses in a biological sample and, on the other hand, to distinguish between genital HPV genotypes, in particular to distinguish between high-risk and low-risk genotypes as well as to type individual genital HPV genotypes.

In conjunction with the present invention, the "carrier" of the nucleotide array means a device comprising a carrier plate with a surface on which a biologically active molecule, for example a nucleic acid, can be immobilized or fixed. Thus, the carrier of the nucleotide array is used to produce a nucleotide array by immobilizing or fixing biologically active molecules, in particular nucleic acids or parts thereof, to the surface of the carrier. The biologically active molecules are arranged on the carrier surface in the form of spots.

The "carrier plate" of the nucleotide array carrier is understood to mean a thin, flat element having, for example, a rectangular shape that is preferably made of a metal, a metal oxide, a plastic, a membrane, glass, ceramic, gel, etc. or a hybrid or combination of these materials. In the context of the present invention, this means that the carrier plate of the carrier is made, for example, completely of one of the materials cited above as examples, or essentially of such materials or that it is made completely of a combination of these materials, or that it essentially contains such materials. The carrier plate or the surface thereof comprises at least approximately 50%, 60%, preferably 70%, more preferably 80%, and most preferably about 100% of one of the above materials cited as examples or of a combination of such materials. In a preferred embodiment the carrier plate of the nucleotide array of the invention comprises approximately 100% plastic.

The surface of the carrier of the carrier of the invention preferably comprises a material that is not smooth, but rather is rough, and/or that is not impermeable, but rather is permeable, or it consists of such material or it contains such a material. In a preferred embodiment of the invention the surface of the carrier comprises a material that is different from that of the carrier plate. For example, the surface may be made of a material such as nitrocellulose, or it may contain nitrocellulose, while the carrier itself is made of a plastic, glass, ceramic, or a metal. In a further preferred embodiment of the invention, the surface of the carrier can also be made of the material used to make the carrier plate. This material preferably has a rough and/or permeable surface.

In a preferred embodiment of the invention, the carrier of the nucleotide array of the invention has a platelet shape, for example in the form of a slide, or in the form of a platelet containing depressions, for example as a chamber slide or as a microtiter plate having dimensions complying with the recommendations of the SBS (Society of Biomolecular Screening).

In accordance with the invention, the first oligonucleotides or nucleic acid molecules, in particular the oligonucleotides having the nucleotide sequences recited in SEQ ID nos. 8 to 135, preferably the oligonucleotides having the nucleotide sequences recited in SEQ ID nos. 19, 32, 41, 44, 48, 82, and 117 to 135, are arranged on the surface of the carrier within a defined analysis area in the form of spots. In the invention the surface of the carrier has at least one control area in addition to the analysis area. The analysis area and the control area may be located at any given defined location on the surface of the carrier.

In the invention, the control area located on the surface of the carrier comprises a control of the orientation of the carrier, a control of amplification, a hybridization control, a sample control and/or a print control.

In one embodiment of the invention, the control of the orientation of the carrier comprises at least the second oligonucleotide or nucleic acid molecule. The second oligonucleotide or nucleic acid molecule is preferably marked, preferably by means of fluorescence. The second oligonucleotide or nucleic acid molecule is preferably disposed in at least three spots on the surface of the carrier so that it is possible to orient the nucleotide array.

In a further embodiment of the invention, the amplification control comprises at least a third oligonucleotide or nucleic acid molecule. Preferably, the third oligonucleotide or nucleic acid molecule is suitable for being used as a probe to detect the presence of an amplification product, whereby the amplification product is obtained by means of an amplification process using a control nucleic acid as the template and a primer pair of the invention, in other words an oligonucleotide having one of the nucleotide sequences recited in SEQ ID nos. 1 to 6 as a forward primer and an oligonucleotide having the nucleotide sequence recited in SEQ ID no. 7 as the reverse primer. In an especially preferred embodiment, the control nucleic acid preferably has a length and a GC content that corresponds to the length and the GC content of the amplification product, which is obtained by means of the amplification process of the invention using the nucleic acid region, in particular that of the E1 gene, of a genital human papilloma virus as the template, an oligonucleotide having one of the nucleotide sequences recited in SEQ ID nos. 1 to 6 as the forward primer, and an oligonucleotide having the nucleotide sequence recited in SEQ ID no. 7 as the reverse primer.

In a further preferred embodiment of the invention, the hybridization control comprises at least a fourth oligonucleotide or nucleic acid molecule. Preferably, at least two to ten spots of the fourth oligonucleotide or nucleic acid molecule are arranged on the carrier surface. In the invention the individual spots of the hybridization control have various quantities of the fourth oligonucleotide or nucleic acid molecule. The hybridization control preferably comprises spots having the dilution series of the fourth oligonucleotide or nucleic acid molecule.

In a further embodiment of the invention, the sample control comprises at least a fifth oligonucleotide or nucleic acid molecule. The fifth oligonucleotide or nucleic acid molecule is preferably suitable for use as a probe to detect a gene that is present in all of the cells of the human organism. In a preferred embodiment, the gene that is detected with the fifth oligonucleotide or nucleic acid molecule is the human ADAT1 gene (t-RNA-specific adenosine deaminase. 1; Gene Bank Accession: NM_012091).

In a further preferred embodiment of the invention, the print control comprises at least a sixth oligonucleotide or nucleic acid molecule. The sixth oligonucleotide or nucleic acid molecule can be arranged in the form of separate spots on the carrier surface. It is particularly preferred that the sixth oligonucleotide or nucleic acid molecule that is being used as the print control, however, be contained in all of the spots located on the nucleotide array carrier, with the exception of the spots of the fourth oligonucleotide/nucleic acid molecule, which is being used as the hybridization control. This means that in this embodiment each spot of the first oligonucleotide/nucleic acid molecule, which is used to detect the presence of an HPV genotype, each spot of the second oligonucleotide/nucleic acid molecule, which is used to check the orientation of the carrier, each spot of the third oligonucleotide/nucleic acid molecule, which is used to check amplification, and each spot of the fifth oligonucleotide/nucleic acid molecule, which is used as a sample control, also includes the sixth oligonucleotide/nucleic acid molecule, which serves as a print control. Preferably, the sixth oligonucleotide or nucleic acid molecule is disposed as a spot on the carrier of the nucleotide array together with the first, second, third and fifth oligonucleotide or nucleic acid molecule respectively in a print step.

The oligonucleotides or nucleic acid molecules fixed on the nucleotide array can be embodied in accordance with the invention as DNA molecules, RNA molecules, PNA molecules, LNA molecules, or hybrid forms thereof.

In a further embodiment of the invention the first, third, fourth, fifth, and sixth oligonucleotides or nucleic acid molecules attached to the carrier do not have any marking, while the second oligonucleotide or nucleic acid molecule, which serve as an orientation control, have a marking, preferably a fluorescent marking.

In a further preferred embodiment of the invention, the nucleotide array has a dot code that can be used to uniquely identify the nucleotide array of the invention and to distinguish the array from other nucleotide chips that, for example, may have the same shape and/or the same or similar arrangement of spots as the nucleotide array of the invention, but which are used for other purposes and therefore have other fixed probes. The dot code of the invention also ensures that, upon software-supported evaluation of the results obtained using the nucleotide array of the invention, the correct software is used for the analysis. Since the relevant information with respect to the nucleotide array is placed directly on the nucleotide chip, additional marking of the chip is no longer necessary. However, the chip may have additional markings. If this marking is lost when the nucleotide array is being used, the dot code of the invention ensures that the chip can be uniquely identified. As provided for in the invention, the dot code is applied to the chip while the chip is being manufactured. Of course, the dot code of the invention can be used not only for the nucleotide array of the invention, which serves to detect and/or identified the genotype of the human papilloma virus, but it can also be used for other nucleotide chips that are used, for example, to identify or detect a specific gene or gene product, to detect specific bacteria, etc.

In the invention, the dot code at the least contains information regarding the intended type of use of the nucleotide array, for example to detect and/or identify the genotype of human papilloma viruses, the batch number, and the chip number. Of course, the dot code of the invention may contain additional information.

In the invention, the type of use is identified by a unique number. For example, the nucleotide array of the invention that is used to detect and/or identify the genotype of human papilloma viruses is identified by the character "#1". A nucleotide chip that is used to identify and/or detect a specific type of bacterium may be identified, for example, by the character "#2". This character can be encoded by means of any given numerical code, for example by means of a binary system, a decimal system, etc. In the 1-of-n coding methods there are n positions, where n is a whole number and where one of the n positions is positive. In the n-ary coding methods, there are m positions that can have n levels of intensity. In the case of binary coding this means that there are two different levels of intensity, so that there are m positions that may either be "1" (positive signal) or "0" (negative signal). In the case of decimal coding, 2 positions can code 100 different numbers, whereby each position can have 10 different levels of intensity.

In the invention, the coding can also comprise a two-dimensional array of spots, wherein a binary coding is achieved in two dimensions corresponding to $2^{(n*m)}$, where n and m represent the dimensions of the array. The dot code can be read out in accordance with the invention in a binary or analog manner. In the case of a binary readout either a "present" or a "not present" is assigned to a specific spot. In contrast to the binary readout, a numerical value is assigned to each spot in the analog readout. This numerical value itself contains information and may relate, for example, to the size of the spot or the signal intensity of the spot.

Additional information on the nucleotide array may also be obtained through the use and/or combination of different amounts of two or more colors on the nucleotide array, whereby the two or more colors may be contained in one or more spots.

In accordance with the invention, when the nucleotide array of the invention is used to detect and/or identify the genotype of a human papilloma virus, whereby in particular the amplification product that is obtained using the process of the invention to amplify a region of a genital human papilloma virus is used, the amplification product that is to be analyzed is used in marked form. The amplification product that is used may be provided with a marking during the amplification reaction, but it may also not be marked until after the completion of the amplification reaction, in other words before the analysis by means of the nucleotide microarray of the invention. A marking of the amplification product during the amplification reaction can be carried out, for example, using marked primers and/or marked nucleotides. In the invention, the amplification product may be marked using fluorescent dyes such as Cy3 or Cy5, biotin, haptenes, antigens, chemical groups, for example through the use of aminoallyl-marker nucleotides, or by applying a marker by means of a succinimide reaction with the aminoallyl-marked nucleotide, radioactive substances, enzymatic markers, etc. The detection of the marked amplification product following the hybridization of the amplification product with a complementary oligonucleotide or nucleic acid molecule on the carrier surface of the nucleotide array of the invention may be carried out, for example, using fluorescence methods, chemoluminescence methods, radiometric methods, densitometry methods, photometric methods, precipitation reactions, enzymatic reactions including enzymatic amplification reactions, SPR, ellipsometry methods, measurement of the index of refraction, measurement of reflectance, and similar processes.

In a preferred embodiment the orientation control, the hybridization control, and the print control may be detected by means of Cy3 in the Cy3 channel, while the amplification control, the sample control, and the HPV genotypes that are to be identified may be detected by means of Cy5 in the Cy5 channel.

The present invention also relates to a kit for detecting and/or identifying genital HPV genotypes comprising at least a first container having at least one primer to amplify nucleic acid regions of a genital human papilloma virus, in particular the regions of the HPV gene E1, and at least one second container having at least one probe to detect and/or identify genital HPV genotypes, in particular to detect an amplified region of the HPV gene E1. The primer used for amplification is selected in the invention from oligonucleotides having one of the nucleotide sequences recited in SEQ ID nos. 1 to 7, oligonucleotides having a nucleotide sequence that is mutated relative to one of the nucleotide sequences recited in SEQ ID nos. 1 to 7, and primer pairs of the invention. The probe for detecting and/or identifying genital HPV genotypes is selected in the invention from oligonucleotides having one of the nucleotide sequences recited in SEQ ID nos. 8 to 135, preferably having one of the nucleotide sequences recited in SEQ ID nos. 19, 32, 41, 44, 48, 82, and 117 to 135, oligonucleotides having a nucleotide sequence that is mutated relative to one of the nucleotide sequences recited in SEQ ID nos. 8 to 135, preferably one of the nucleotide sequences recited in SEQ ID nos. 19, 32, 41, 44, 48, 82, and 117 to 135, oligonucleotides having a nucleotide sequence that is complementary to one of the nucleotide sequences recited in SEQ ID nos. 8 to 135, preferably to one of the nucleotide sequences recited in SEQ ID nos. 19, 32, 41, 44, 48, 82, and 117 to 135 or a mutated nucleotide sequence thereof, or nucleic acid molecules that have one of the nucleotide sequences recited in SEQ ID nos. 8 to 135, preferably one of the nucleotide sequences recited in SEQ ID nos. 19, 32, 41, 44, 48, 82, or 117 to 135, a mutated nucleotide sequence thereof, or a complementary nucleotide sequence thereof.

In a preferred embodiment of the invention, the kit has at least 29 second containers having at least 29 different probes to detect and/or identify the HPV6, in particular HPV6b, HPV11, HPV16, HPV18, HPV26, HPV31, HPV33, HPV34, HPV35, in particular HPV35h, HPV39, HPV40, HPV42, HPV43, HPV44, HPV45, HPV51, HPV52, HPV53, HPV54, HPV56, HPV58, HPV59, HPV61, HPV66, HPV67, HPV68, HPV70, HPV73, and HPV82 genotypes, where each container contains at least one probe, and where each of the probes contained in a container can only detect a specific HPV genotype. Especially preferred is a kit having at least 24 second containers having at least 24 different probes to detect and/or identify the HPV6, in particular HPV6b, HPV11, HPV16, HPV18, HPV31, HPV33, HPV35, in particular HPV35h, HPV39, HPV40, HPV42, HPV43, HPV44, HPV45, HPV51, HPV52, HPV53, HPV56, HPV58, HPV59, HPV66, HPV68, HPV70, HPV73, and HPV82 genotypes.

If, for example, the probes contained in a container are to be used to detect the HPV6 genotype, in particular the HPV6b genotype, the container may contain an oligonucleotide having the nucleotide sequence recited in SEQ ID nos. 8, 9, or 117, preferably the nucleotide sequence recited in SEQ ID no. 117, an oligonucleotide having a nucleotide sequence that is mutated relative to the nucleotide sequence of SEQ ID nos. 8, 9, or 117, an oligonucleotide having a nucleotide sequence that is complementary to SEQ ID nos. 8, 9, or 117, or a mutated sequence thereof, a nucleic acid molecule that has the sequence of SEQ ID nos. 8, 9, or 117, preferably the sequence of SEQ ID no. 117, a mutated sequence thereof, or a complementary sequence thereof, or a mixture of these oligonucleotides and/or nucleic acid molecules. However, each container preferably does not contain a mixture, but rather only a single species of oligonucleotide or nucleic acid molecule.

The present invention also relates to a kit for detecting and/or identifying genital HPV genotypes comprising at least a first container having at least a primer for amplifying nucleic acid regions of the genital human papilloma virus, in particular the regions of the HPV gene E1, and a nucleotide array of the invention for detecting and/or identifying genital HPV genotypes, in particular to detect an amplified region of the HPV gene E1. The primer used for the amplification is selected in the invention from oligonucleotides having one of the nucleotide sequences recited in SEQ ID nos. 1 to 7, oligonucleotides having a nucleotide sequence that is mutated relative to one of the nucleotide sequences recited in SEQ ID nos. 1 to 7, and the primer pairs of the invention. The nucleotide array of the kit of the invention preferably comprises oligonucleotides having one of the nucleotide sequences recited in SEQ ID nos. 8 to 135, more preferably one of the nucleotide sequences recited in SEQ ID nos. 19, 32, 41, 44, 48, 82, and 117 to 135, oligonucleotides having a nucleotide sequence that is mutated relative to one of the nucleotide sequences recited in SEQ ID nos. 8 to 135, preferably relative to one of the nucleotide sequences recited in SEQ ID nos. 19, 32, 41, 44, 48, 82, and 117 to 135, oligonucleotides having a nucleotide sequence that is complementary to one of the nucleotide sequences recited in SEQ ID nos. 8 to 135, preferably to one of the nucleotide sequences recited in SEQ ID nos. 19, 32, 41, 44, 48, 82, and 117 to 135, or a mutated nucleotide sequence thereof, and/or nucleic acid molecules that comprise one of the nucleotide sequences recited in SEQ ID nos. 8 to 135, preferably one of the nucleotide sequences recited in SEQ ID nos. 19, 32, 41, 44, 48, 82, and 117 to 135, a mutated nucleotide sequence thereof, or a complementary nucleotide sequence thereof.

In a preferred embodiment of the invention, the kit of the invention comprises at least two first containers, wherein one container thereof contains equimolar amounts of the oligonucleotides having the nucleotide sequences recited in SEQ ID nos. 2 to 6, and the other container contains the oligonucleotide having the nucleotide sequence recited in SEQ ID no. 7. In an alternative embodiment, the kit of the invention comprises 6 first containers, where five containers in each case contain one of the oligonucleotides having the nucleotide sequences recited in SEQ ID nos. 2 to 6, and the sixth container contains the oligonucleotide having the nucleotide sequence recited in SEQ ID no. 7.

The kit of the invention can also comprise a container having a controlled nucleic acid that can be amplified, using an oligonucleotide having one of the nucleotide sequences recited in SEQ ID nos. 1 to 6 as the forward primer and using an oligonucleotide having the nucleotide sequence recited in SEQ ID no. 7 as the reverse primer.

Of course, the present invention also relates to the use of an oligonucleotide having one of the nucleotide sequences set forth in SEQ ID nos. 8 to 135, preferably one of the nucleotide sequences recited in SEQ ID nos. 19, 32, 41, 44, 48, 82, and 117 to 135 of an oligonucleotide whose nucleotide sequence is mutated relative to one of the nucleotide sequences recited in SEQ ID nos. 8 to 135, in particular one of the nucleotide sequences recited in SEQ ID nos. 19, 32, 41, 44, 48, 82, and 117 to 135, of an oligonucleotide whose nucleotide sequence is complementary to one of the nucleotide sequences set forth in SEQ ID nos. 8 to 135, in particular to one of the nucleotide sequences set forth in SEQ ID nos. 19, 32, 41, 44, 48, 82, and 117 to 135, or a mutated nucleotide sequence thereof, or of a nucleic acid molecule that comprises one of the nucleotide sequences set forth in SEQ ID nos. 8 to 135, in particular one of the nucleotide sequences recited in SEQ ID nos. 19, 32, 41, 44, 48, 82, and 117 to 135, a mutated sequence thereof, or a complementary sequence thereof, to detect or identify a genital HPV genotype, in other words to type a papilloma virus whose presence was preferably already detected in a biological sample.

The present invention also relates to the use of an oligonucleotide having one of the nucleotide sequences recited in one of the SEQ ID nos. 1 to 7, and/or of an oligonucleotide whose nucleotide sequence is mutated relative to one of the nucleotide sequences recited in SEQ ID nos. 1 to 7, or one of the primer pairs of the invention to amplify a nucleic acid region of a genital human papilloma virus, wherein the preferred embodiment of the nucleic acid region that is to be amplified is a region of the HPV gene E1.

The present invention also relates to the use of an oligonucleotide having one of the nucleotide sequences set forth in SEQ ID nos. 1 to 135 of an oligonucleotide whose nucleotide sequence is mutated relative to one of the nucleotide sequences recited in SEQ ID nos. 1 to 135, of an oligonucleotide that has any nucleotide sequence that is complementary to one of the nucleotide sequences recited in SEQ ID nos. 8 to 135, or of a mutated sequence thereof, of a nucleic acid molecule that comprises one of the nucleotide sequences recited in SEQ ID nos. 8 to 135, a mutated sequence thereof, or a complementary sequence thereof, or of a primer pair of the invention for the diagnosis and/or early detection of diseases caused by genital human papilloma viruses.

The present invention also relates to the use of an oligonucleotide having one of the nucleotide sequences recited in SEQ ID nos. 1 to 135, in particular one of the nucleotide sequences recited in SEQ ID nos. 1 to 7, 19, 32, 41, 44, 48, 82, and 117 to 135, of an oligonucleotide whose nucleotide sequence is mutated relative to one of the nucleotide sequences set forth in SEQ ID nos. 1 to 135, in particular to one of the nucleotide sequences recited in SEQ ID nos. 1 to 7, 19, 32, 41, 44, 48, 82, and 117 to 135, of an oligonucleotide that has a nucleotide sequence that is complementary to one of the nucleotide sequences recited in SEQ ID nos. 8 to 135, in particular to one of the nucleotide sequences recited in SEQ ID nos. 1 to 7, 19, 32, 41, 44, 48, 82, and 117 to 135, or a mutated sequence thereof, of a nucleic acid molecule that comprises one of the nucleotide sequences recited in SEQ ID nos. 8 to 135, in particular one of the nucleotide sequences recited in SEQ ID nos. 19, 32, 41, 44, 48, 82, and 117 to 135, a mutated sequence thereof, or a complementary sequence thereof, or of a primer pair of the invention to prepare a means for the diagnosis of diseases that are caused by genital human papilloma viruses.

The means that is prepared may, for example, be the kit of the invention or a nucleotide array of the invention.

The present invention is explained in greater detail by the following sequence protocol, the following figures, and the following examples.

The sequence protocol is part of this description, and it contains sequences SEQ ID nos. 1 to 135.

SEQ ID no. 1 to SEQ ID no. 6 show the sequences of oligonucleotides that are suitable for use as forward primers to amplify regions of the HPV gene E1. The oligonucleotides used as forward primers having the nucleotide sequences recited in SEQ ID nos. 2 to 6 are referred to below as Loma 1, Loma 2, Loma 3, Loma 4, and Loma 5, respectively.

SEQ ID no. 7 shows the sequence of an oligonucleotide that is suitable for use as a reverse primer for amplifying regions of the HPV gene E1. The oligonucleotide that has the nucleotide sequence recited in SEQ ID no. 7 and that is used as the reverse primer is referred to below as Loma-rev.

SEQ ID nos. 8, 9, and 117 show the sequences of oligonucleotides that are suitable for use to detect and identify the HPV6 genotype, in particular the HPV6b genotype.

SEQ ID no. 10 to SEQ ID no. 17, and SEQ ID no. 118 show the sequences of oligonucleotides that are suitable for detecting and identifying the HPV11 genotype.

SEQ ID no. 18 to SEQ ID no. 20 show the sequences of oligonucleotides that are suitable for detecting and identifying the HPV16 genotype.

SEQ ID no. 21 to SEQ ID no. 24 and SEQ ID no. 119 show the sequences of oligonucleotides that are suitable for detecting and identifying the HPV18 genotype.

SEQ ID no. 25 to SEQ ID no. 28 show the sequences of oligonucleotides that are suitable for detecting and identifying the HPV26 genotype.

SEQ ID no. 29 to SEQ ID no. 31 and SEQ ID no. 120 show the sequences of oligonucleotides that are suitable for detecting and identifying the HPV31 genotype.

SEQ ID no. 32 to SEQ ID no. 34 show the sequences of oligonucleotides that are suitable for detecting and identifying the HPV33 genotype.

SEQ ID no. 35 to SEQ ID no. 39 show the sequences of oligonucleotides that are suitable for detecting and identifying the HPV34 genotype.

SEQ ID no. 40 to SEQ ID no. 41 show the sequences of oligonucleotides that are suitable for detecting and identifying the HPV35h genotype.

SEQ ID no. 42 to SEQ ID no. 46 show the sequences of oligonucleotides that are suitable for detecting and identifying the HPV39 genotype.

SEQ ID no. 47 to SEQ ID no. 50 show the sequences of oligonucleotides that are suitable for detecting and identifying the HPV40 genotype.

SEQ ID no. 51, SEQ ID no. 52, and SEQ ID no. 121 show the sequences of oligonucleotides that are suitable for detecting and identifying the HPV42 genotype.

SEQ ID no. 122 shows the sequence of an oligonucleotide that is suitable for detecting and identifying the HPV43 genotype.

SEQ ID no. 53, SEQ ID no. 55, and SEQ ID no. 123 show the sequences of oligonucleotides that are suitable for detecting and identifying the HPV44 genotype.

SEQ ID no. 56 to SEQ ID no. 61, and SEQ ID no. 124 show the sequences of oligonucleotides that are suitable for detecting and identifying the HPV45 genotype.

SEQ ID no. 62 to SEQ ID no. 64, and SEQ ID no. 125 show the sequences of oligonucleotides that are suitable for detecting and identifying the HPV51 genotype.

SEQ ID no. 65 to SEQ ID no. 67, and SEQ ID no. 126 show the sequences of oligonucleotides that are suitable for detecting and identifying the HPV52 genotype.

SEQ ID no. 68 to SEQ ID no. 73, and SEQ ID no. 127 show the sequences of oligonucleotides that are suitable for detecting and identifying the HPV53 genotype.

SEQ ID no. 74 to SEQ ID no. 77 show the sequences of oligonucleotides that are suitable for detecting and identifying the HPV54 genotype.

SEQ ID no. 78 to SEQ ID no. 81, and SEQ ID no. 128 show the sequences of oligonucleotides that are suitable for detecting and identifying the HPV56 genotype.

SEQ ID no. 82 to SEQ ID no. 86 show the sequences of oligonucleotides that are suitable for detecting and identifying the HPV58 genotype.

SEQ ID no. 87 and SEQ ID no. 129 show the sequences of oligonucleotides that are suitable for detecting and identifying the HPV59 genotype.

SEQ ID no. 88 to SEQ ID no. 94 show the sequences of oligonucleotides that are suitable for detecting and identifying the HPV61 genotype.

SEQ ID no. 95 to SEQ ID no. 97, and SEQ ID no. 130 show the sequences of oligonucleotides that are suitable for detecting and identifying the HPV66 genotype.

SEQ ID no. 98 to SEQ ID no. 102 show the sequences of oligonucleotides that are suitable for detecting and identifying the HPV67 genotype.

SEQ ID no. 103 to SEQ ID no. 105, SEQ ID no. 131, and SEQ ID no. 132 show the sequences of oligonucleotides that are suitable for detecting and identifying the HPV68 genotype.

SEQ ID no. 106 to SEQ ID no. 108, and SEQ ID no. 133 show the sequences of oligonucleotides that are suitable for detecting and identifying the HPV70 genotype.

SEQ ID no. 109 to SEQ ID no. 112, and SEQ ID no. 134 show the sequences of oligonucleotides that are suitable for detecting and identifying the HPV73 genotype.

SEQ ID no. 113 to SEQ ID no. 116, and SEQ ID no. 135 show the sequences of oligonucleotides that are suitable for detecting and identifying the HPV82 genotype.

FIG. 1 shows the results of an acrylamide gel electrophoresis (non-denaturing) of amplification products that were obtained using the primers of the invention and the DNAs of various papilloma viruses as templates. An equimolar mixture of the primers Loma 1, Loma 2, Loma 3, Loma 4, and Loma 5 (which correspond to the oligonucleotides having the nucleotide sequences recited in SEQ ID nos. 2 to 6) was used as the forward primer. The primer Loma-rev (which corresponds to the oligonucleotide having the nucleotide sequence recited in SEQ ID no. 7) was used as the reverse primer. Plasmids that contain the entire HPV6, HPV16, HPV58, HPV59, and HPV 82 genome, respectively, were used as the template. Human DNA was used as the negative control.

FIG. 1A: Nucleic acid size standard (track 1), amplification product using HPV6 DNA (track 2), amplification product using HPV16 DNA (track 3), FIG. 1B: Amplification product using HPV58 DNA (track 4), amplification product using HPV59 DNA (track 5), amplification product using HPV82 DNA (track 6), amplification reaction using human DNA (track 7; negative control), nucleic acid size standard (track 8).

Figure 2:
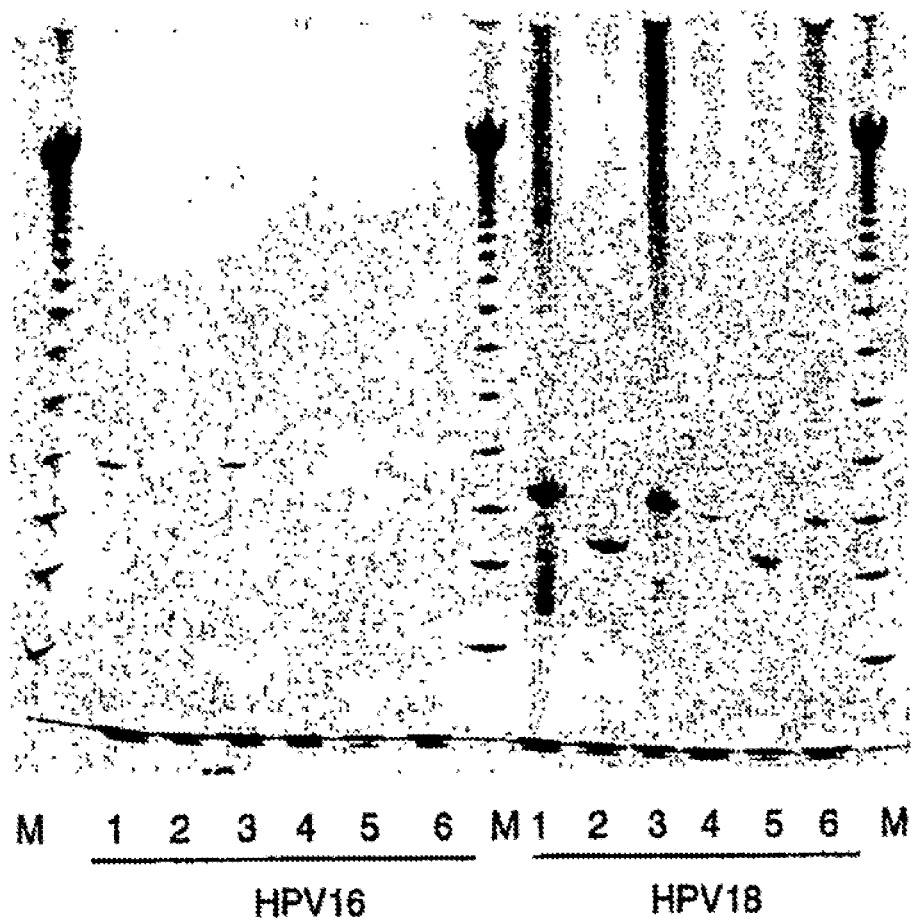

FIG. 2 shows the results of an acrylamide gel electrophoresis (non-denaturing) of amplification products that were obtained using HPV16 or HPV18 DNA as the templates. The primer combination of the invention Loma1-5/Loma-rev (combination 1), the primer combination Loma1-5/P2 (SEQ ID No 2 from DE 100 09 143 A1) (combination 2), the primer combination Loma1-5/P3 (SEQ ID no. 3 from DE 100 09 143 A1) (combination 3), the primer combination P1 (SEQ ID no. 1 from DE 100 09 143 A1)/Loma-rev (combination 4), the primer combination P1/P2 (combination 5), and the primer combination P1/P3 (combination 6) were used as the primers. M=DNA size standard (123 bp ladder), 1=primer combination 1, 2=primer combination 2, 3=primer combination 3, 4=primer combination 4, 5=primer combination 5, 6=primer combination 6.

Figure 3:
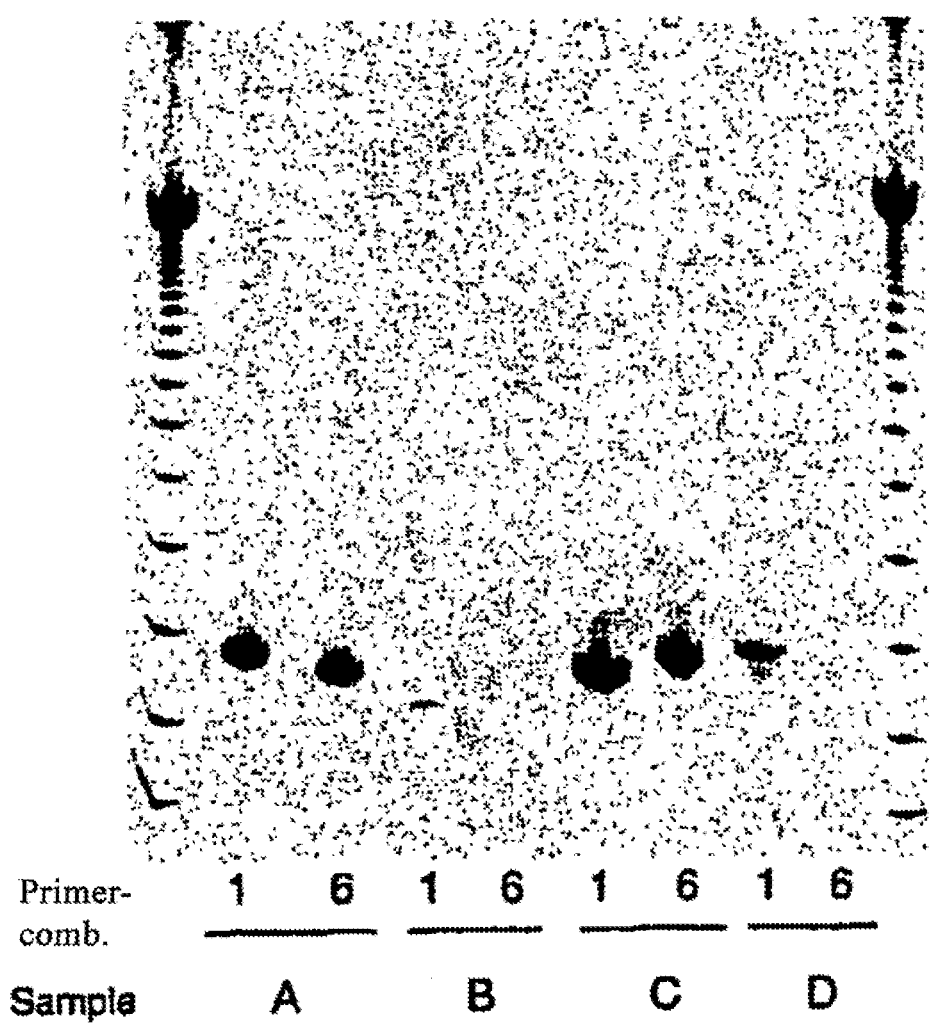

FIG. 3 shows the results of an acrylamide gel electrophoresis (non-denaturing) of amplification products that were obtained using patient samples. The primer combinations 1 (Loma1-5/Loma-rev) and 6 (P1/P3) were used as the primers. A=patient sample that was classified by means of in-situ hybridization as being HPV16-positive, B=patient sample, that was classified by means of in-situ hybridization as being HPV73 positive, C=patient sample, that was classified by means of in-situ hybridization as being negative, D=patient sample that was classified by means of in-situ hybridization as being HPV33-positive. A single DNA size standard (123 bp ladder) is plotted in each of the left outer and right outer tracks.

FIG. 4a shows the design of a nucleotide array or nucleotide chip of the invention wherein there are located on the surface of the microarray carrier a control to check the orientation of the microarray carrier (OC), a hybridization control (HC), a PCR control (AC), a sample control (SC), as well as probes to type the HPV genotypes. The microarray also has spots for chip coding. The hybridization control and the PCR control may be designed as dilution series of the corresponding oligonucleotides. Numbers indicate the names of the HPV types for which the respective probe is specific. A print control is also located on all spots with the exception of the orientation control and the hybridization control.

Figure 4B:
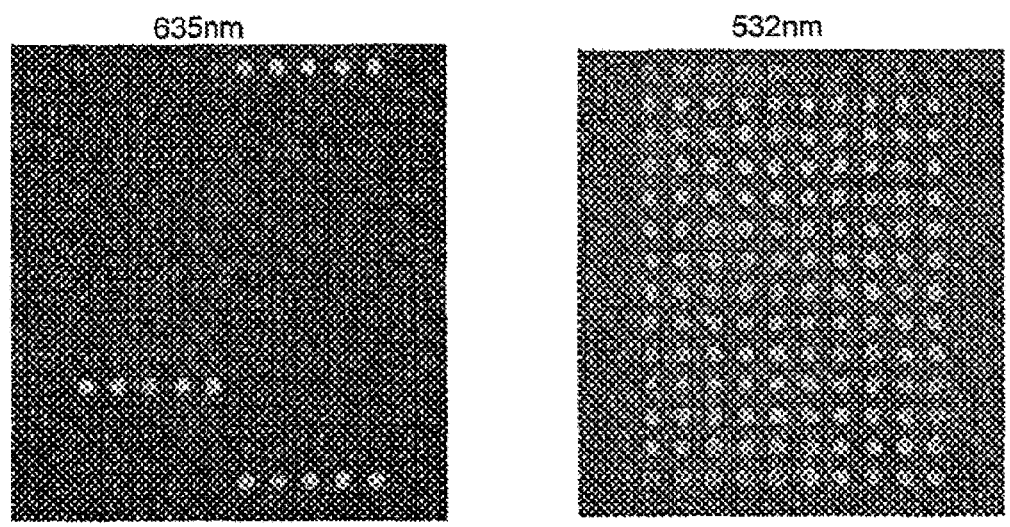

FIG. 4b shows a specific hybridization for HPV42. OC, HC, and print controls are detected by means of fluorescent light upon excitation with light having a wavelength of 532 nm. AC, SC, and the HPC-specific signals are detected by means of fluorescent light after excitation with light having a wavelength of 635 nm.

EXAMPLE 1

Amplification of HPV DNA Using the Primers Loma/Loma-Rev of the Invention

In order to achieve the amplification, plasmids having the genomes of HPV6, HPV16, HPV58, HPV 59, and HPV 82 were used as the template. These plasmids contain the entire genome of the respective HPV type. Human DNA was used as a negative control. Table 1 shows the composition of the reaction mixture and the concentration of the primers that were used.

TABLE 1

| Solution | mL | Final Concentration |
| --- | --- | --- |
| H$_2$O | 12.6 | |
| 10× PCR buffer (for AmpliTaq Gold; without MgCl$_2$) | 2 | 1x |
| 25 mM MgCl$_2$ | 2 | 2.5 mM |
| 25 mM dNTP (f.c.: 0.25 mM) | 0.2 | 0.25 mM |
| Loma mix with 4 pmole/μL of each of the primers Loma 1-Loma5 | 1 | 0.2 pmole/μL of each of the 5 Loma primers |
| 20 pmole/μL Loma-rev Cy5-marked | 1 | 1 pmole/μL |
| 5 u/μL Ampli Taq Gold | 0.2 | 0.05 u/μL |
| DNA template (HPV plasmid) | 1 | |
| Total | 20 | |

The PCR was performed under the following temperature conditions. First, the reaction mixture was heated to a temperature of 95° C., during which time the temperature was increased at a rate of 1° C./sec. The temperature of the reaction mixture was held at 95° C. for 10 minutes. Then the reaction mixture was subjected to the following temperature conditions: per cycle 30 seconds at 95° C., 30 seconds at 55° C., and 1 minute at 72° C. A total of 40 cycles were performed. After completion of the 40 cycles, the temperature of the reaction mixture was held for 5 minutes at 72° C., and then cooled to 4° C.

In each case 2 μL of the resulting PCR products were separated on a non-denaturing acrylamide gel and were made visible by means of a silver stain. The results are shown in FIGS. 1A and 1B. Sequence differences between the various HPV types result in different flow properties in the non-denaturing gel. As can be seen from FIG. 1, the control DNA, which was the negative control, did not receive PCR product.

EXAMPLE 2

PCR Amplification Using the Primers of the Invention in Comparison with PCR Amplification Using Prior-Art Primers In this test, the suitability of the forward and reverse primers of the invention in the amplification of nucleic acid regions of genital HPV viruses was to be determined in comparison with PCR amplification using the prior-art primer pairs.

In DE 100 09 143 A1 two PCR primer systems are described. These primer systems comprise either the primer having sequence ID no. 1 (referred to below as P1) and the primer having SEQ ID no. 2 (referred to below as P2), or the primer having SEQ ID no. 1 and SEQ ID no. 3 (referred to hereafter also as P3). Since only those PCR systems that have primers P1 and P3 are suitable for typing papilloma viruses, this system is the definitive basis for comparing the Loma/Loma-one primer system of the invention. Because of the position of the primers on the HPV genome, both primer P1 as well as the equimolar primer mixture of the invention, comprising the primers Loma 1, Loma 2, Loma 3, Loma 4, and Loma 5 are combined with each of the primers P2, P3, and Loma-rev in order to obtain a PCR product. All six possible primer combinations were investigated in the test. The primer combinations that were used are shown in Table 2.

The HPV16 plasmid having the genome of the HPV16 type, as well as the HPV18 DNA, which had been extracted from HeLa cells, were used as the DNA templates. The concentrations of the respective templates were adjusted in preliminary tests so that they would come close to the limit of amplifiability with the Loma/Loma-rev primer system, but would still produce a distinct PCR amplification product. The PCR was performed under the following temperature conditions: Ramp: 1° C./sec, hold temperature at 95° C. for 10 minutes, 40 cycles, each of 30 sec at 95° C., 30 sec at 55° C., 1 min at 72° C., thereafter hold temperature at 72° C. for 5 min, and cool to 4° C.

TABLE 2

| Primer Combination | Forward Primer | Reverse Primer |
| --- | --- | --- |
| 1 | Loma 1-5 | Loma-rev |
| 2 | Loma 1-5 | SEQ ID no. 2 from DE 100 09 143 (P2) |
| 3 | Loma 1-5 | SEQ ID no. 3 from DE 100 09 143 (P3) |
| 4 | SEQ ID no. 1 from DE 100 09 143 (P1) | Loma-rev |
| 5 | SEQ ID no. 1 from DE 100 09 143 (P1) | SEQ ID no. 2 from DE 100 09 143 (P2) |
| 6 | SEQ ID no. 1 from DE 100 09 143 (P1) | SEQ ID no. 3 from DE 100 09 143 (P3) |

The results obtained with the above primer combinations are shown in FIG. 2. Primer combination 1 produces a PCR product both with the amplification of the HPV16 DNA as well as with the amplification of the HPV18 DNA. Primer combination 2 does not produce a detectable PCR product in the case of the HPV16 DNA. Primer combination 3 yields a PCR product with the two tested nucleic acid templates. Primer combinations 4 to 6 did not produce any PCR product at the selected dilution of the HPV16 DNA, and with the HPV18 DNA they produce a significantly smaller amount of amplification product than primer combinations 1 to 3.

EXAMPLE 3

Amplification of HPV Templates from Patient Samples

Using DNA extracts from four samples taken from patients (paraffin sections of cervical samples), PCR reactions were performed with primer combinations 1 and 6 (see Table 2). These samples were previously tested for HPV infections by means of in-situ hybridization. The results are shown in Table 3 and FIG. 3.

TABLE 3

| Patient Sample | Results of In-Situ Hybridization | Results of PCR Loma1-5/Loma-rev | Results of PCR SEQ ID no. 1 (P1)/SEQ ID no. 3 (P3) |
| --- | --- | --- | --- |
| A | HPV16 | + | + |
| B | HPV73 | + | − |
| C | Negative | + | + |
| D | HPV33 | + | + |

The results clearly show that both PCR reactions are more sensitive than the hybridization in the case of Sample C because this sample was positive with both primer pairs. Samples B and D are only positive with the Loma/Loma-rev primers of the invention, but not with the prior-art primer combination P1/P3.

EXAMPLE 4

Hybridization of an Amplification Product of the Loma Primers on a Nucleotide Array of the Invention To achieve the amplification a plasmid having a portion of the genome of HPV42 was used as a template, mixed with human DNA, and with a plasmid that contains a synthetic DNA construct that contains a short section of the genome of the phage lambda surrounded on the sides by binding sites for the primers of SEQ ID no. 4 and SEQ ID no. 7. The probe for the amplification control on the nucleotide array is specific for this section of the phage lambda genome.

In the PCR mixture, primers for amplifying a section from the human ADAT1 gene were used in addition to the Loma primers.

One of the primers for the amplification of the human ADAT1 gene and the primer of SEQ ID no. 6 are marked with the fluorescent dye Cy5.

After successful DNA amplification, 5 µL of the PCR product was mixed with 30 µL hybridization buffer (0.5% lauryl sarcosine, 0.225 M NaCl, 0.225 M sodium citrate, 20 nm of a Cy3-marked oligonucleotide that is complementary to the hybridization and print control on the nucleotide array). The mixture was denatured for 3 min at 95° C., cooled on ice water, and hybridized for 10 minutes at 50° C. on the nucleotide array. The nucleotide array was washed three times, in each case for 20 seconds at 50° C. in washing buffer (0.2% sodium dodecyl sulfate, 0.3 M NaCl, 0.03 M sodium citrate, pH 7). In a conventional commercially available microarray scanner, the nucleotide array was scanned upon excitation with light having wavelengths of 532 nm and 635 nm. The result is shown in FIG. 4b. FIG. 4a shows the position of the probes on the nucleotide array being used.

What is claimed is:

1. A nucleotide array and primer mixture, together as a kit, for detecting and/or identifying the genotype of a human papilloma virus contained in a biological sample:

the nucleotide array comprising a solid carrier having a surface and at least one first oligonucleotide or nucleic acid molecule bound to the carrier surface that is suitable for use as a probe for testing the HPV gene E1 or a portion thereof to detect and/or identify a genital human HPV genotype, the at least one first oligonucleotide or nucleic acid molecule selected from the group consisting of:

a) HPV genotype-specific oligonucleotides having the nucleotide sequences recited in SEQ ID Nos. 8 to 135, b) oligonucleotides that have a nucleotide sequence that is mutated relative to one of the oligonucleotides of a), namely, a deletion or addition of 1 to 10 nucleotides or a substitution of 1 to 3 nucleotides in one of the nucleotide sequences recited in a), c) oligonucleotides that have a nucleotide sequence that is complementary over its entire length to the nucleotide sequence of an oligonucleotide of a) or b), d) nucleic acid molecules comprising at least one region that has one of the nucleotide sequences recited in a) to c) and one or more additional regions having a total length of at least one nucleotide, and e) mixtures of the oligonucleotides of a) to c) and/or of the nucleic acid molecules of d); and the primer mixture comprising:

(1) a mixture of oligonucleotides as a forward primer, the mixture including at least two oligonucleotides selected from the group consisting of (i) to (v):

(i) an oligonucleotide having the nucleotide sequence 5'-CAR GCN AAA TAT KTR AAA GAT TGT G-3' (SEQ ID no. 2), or an oligonucleotide that has a nucleotide sequence that is mutated relative to the SEQ ID no. 2, obtained by the:
(a) deletion of 1 to 10 nucleotides in the nucleotide sequence of SEQ ID no. 2,
(b) addition of 1 to 10 nucleotides in the nucleotide sequence of SEQ ID no. 2, and/or
(c) substitution of 1 to 3 nucleotides in the nucleotide sequence of SEQ ID no. 2, (ii) an oligonucleotide having the nucleotide sequence 5'-CAR GCA AAA TAT GTW AAG GAT TGT G-3' (SEQ ID no. 3) or an oligonucleotide that has a nucleotide sequence that is mutated relative to the SEQ ID no. 3, obtained by the:
(a) deletion of 1 to 10 nucleotides in the nucleotide sequence of SEQ ID no. 3,
(b) addition of 1 to 10 nucleotides in the nucleotide sequence of SEQ ID no. 3, and/or
(c) substitution of 1 to 3 nucleotides in the nucleotide sequence of SEQ ID no. 3, (iii) an oligonucleotide having the nucleotide sequence 5'-CAR GCW AAA ATT GTA AAR GAT TGT G-3' (SEQ ID no. 4), or an oligonucleotide that has a nucleotide sequence that is mutated relative to the SEQ ID no. 4, obtained by the:
(a) deletion of 1 to 10 nucleotides in the nucleotide sequence of SEQ ID no. 4,
(b) addition of 1 to 10 nucleotides in the nucleotide sequence of SEQ ID no. 4, and/or (c) substitution of 1 to 3 nucleotides in the nucleotide sequence of SEQ ID no. 4,
(iv) an oligonucleotide having the nucleotide sequence 5'-CAA GCA AAA ATA GTA AAR GAC TGT G-3' (SEQ ID no. 5), or an oligonucleotide that has a nucleotide sequence that is mutated relative to the SEQ ID no. 5, obtained by the:
(a) deletion of 1 to 10 nucleotides in the nucleotide sequence of SEQ ID no. 5,
(b) addition of 1 to 10 nucleotides in the nucleotide sequence of SEQ ID no. 5, and/or
(c) substitution of 1 to 3 nucleotides in the nucleotide sequence of SEQ ID no. 5,
(v) an oligonucleotide having the nucleotide sequence 5'-CAR GCA AAA TAT GTA AAA GAC TGT G-3' (SEQ ID no. 6), or an oligonucleotide that has a nucleotide sequence that is mutated relative to the SEQ ID no. 6, obtained by the:
(a) deletion of 1 to 10 nucleotides in the nucleotide sequence of SEQ ID no. 6,
(b) addition of 1 to 10 nucleotides in the nucleotide sequence of SEQ ID no. 6, and/or
(c) substitution of 1 to 3 nucleotides in the nucleotide sequence of SEQ ID no. 6; and
(2) an oligonucleotide as a reverse primer having the nucleotide sequence 5'- ARY GGY TSY ARC CAA AAR TGR CT-3' (SEQ ID no. 7), or an oligonucleotide that has a nucleotide sequence that is mutated relative to the SEQ ID no. 7, obtained by the:
(a) deletion of 1 to 10 nucleotides in the nucleotide sequence of SEQ ID no. 7,
(b) addition of 1 to 10 nucleotides in the nucleotide sequence of SEQ ID no. 7, and/or
(c) substitution of 1 to 3 nucleotides in the nucleotide sequence of SEQ ID no. 7,
wherein R=A or G, W=T or A, K=T or G, I=inosine, N=A, T, G, or C, D=A, T, or G, Y=C or T, and S=C or G.

2. The nucleotide array and primer mixture kit of claim 1, wherein the carrier is platelet-shaped, in the form of a microscope slide, or is platelet-shaped with depressions as a chamber slide or as a microtiter plate.

3. The nucleotide array and primer mixture kit of claim 1, wherein the first oligonucleotides or nucleic acid molecules on the surface of the carrier are located in a defined analysis area.

4. The nucleotide array and primer mixture kit of claim 2, wherein the first oligonucleotides or nucleic acid molecules on the surface of the carrier are located in a defined analysis area.

5. The nucleotide array and primer mixture kit of claims 1, wherein the surface of the carrier has a control area.

6. The nucleotide array and primer mixture kit of claims 2, wherein the surface of the carrier has a control area.

7. The nucleotide array and primer mixture kit of claims 3, wherein the surface of the carrier has a control area.

8. The nucleotide array and primer mixture kit of claim 5, wherein the control area comprises a control for orienting the carrier, an amplification control, a hybridization control, a sample control, and/or a print control.

9. The nucleotide array and primer mixture kit of claim 6, wherein the control area comprises a control for orienting the carrier, an amplification control, a hybridization control, a sample control, and/or a print control.

10. The nucleotide array and primer mixture kit of claim 7, wherein the control area comprises a control for orienting the carrier, an amplification control, a hybridization control, a sample control, and/or a print control.

11. The nucleotide array and primer mixture kit of claim 8, wherein the control for orienting the carrier comprises at least one second oligonucleotide or nucleic acid molecule.

12. The nucleotide array and primer mixture kit of claim 9, wherein the control for orienting the carrier comprises at least one second oligonucleotide or nucleic acid molecule.

13. The nucleotide array and primer mixture kit of claim 10, wherein the control for orienting the carrier comprises at least one second oligonucleotide or nucleic acid molecule.

14. The nucleotide array and primer mixture kit of claim 11, wherein the second oligonucleotide is a fluorescent oligonucleotide, and the control for orienting the carrier comprises at least three spots of the fluorescent oligonucleotide.

15. The nucleotide array and primer mixture kit of claim 12, wherein the second oligonucleotide is a fluorescent oligonucleotide, and the control for orienting the carrier comprises at least three spots of the fluorescent oligonucleotide.

16. The nucleotide array and primer mixture kit of claim 13, wherein the second oligonucleotide is a fluorescent oligonucleotide, and the control for orienting the carrier comprises at least three spots of the fluorescent oligonucleotide.

17. The nucleotide array and primer mixture kit of claim 14, wherein the amplification control comprises at least one third oligonucleotide or nucleic acid molecule.

18. The nucleotide array and primer mixture kit of claim 15, wherein the amplification control comprises at least one third oligonucleotide or nucleic acid molecule.

19. The nucleotide array and primer mixture kit of claim 16, wherein the amplification control comprises at least one third oligonucleotide or nucleic acid molecule.

20. The nucleotide array and primer mixture kit of claim 17, wherein the third oligonucleotide or nucleic acid molecule is suitable for use as a probe for detecting an amplification product that is obtained by means of an amplification process using a control nucleic acid as the template and a primer pair comprising a forward primer and a reverse primer, wherein the forward primer is selected from the group consisting of:
a) an oligonucleotide that may be used as a primer, in particular a forward primer, to amplify a nucleic acid region of a genital human papilloma virus (HPV) and that has the sequence 5'-CAR GCI AAA WWW KTD AAR GAY TGT G-3' (SEQ ID no. 136) or 5'- CAR GCN AAA WWW KTD AAR GAY TGT G-3' (SEQ ID no. 1), or any of the following sequences:
(i) an oligonucleotide having the nucleotide sequence 5'-CAR GCI AAA TAT KTR AAA GAT TGT G-3' (SEQ ID no. 137) or 5'-CAR GCN AAA TAT KTR AAA GAT TGT G-3' (SEQ ID no. 2),
(ii) an oligonucleotide having the nucleotide sequence 5'-CAR GCA AAA TAT GTW AAG GAT TGT G-3' (SEQ ID no. 3),
(iii) an oligonucleotide having the nucleotide sequence 5'-CAR GCW AAA ATT GTA AAR GAT TGT G-3' (SEQ ID no. 4),
(iv) an oligonucleotide having the nucleotide sequence 5'-CAA GCA AAA ATA GTA AAR GAC TGT G-3' (SEQ ID no. 5),
(v) an oligonucleotide having the nucleotide sequence 5'-CAR GCA AAA TAT GTA AAA GAC TGT G-3' (SEQ ID no. 6), or
(vi) an oligonucleotide having the nucleotide sequence 5'-ARY GGY TSY ARC CAA AAR TGR CT-3' (SEQ ID no. 7), wherein R=A or G, W=T or A, K=T or G, I=inosine, N=A, T, G, or C, D=A, T, or G, Y=C or T, and S=C or G, b) an oligonucleotide of a) that has a nucleotide sequence that is mutated relative to one of the nucleotide sequences recited in SEQ ID nos. 136, 137 or 2-7, which may be obtained by the:
  (i) deletion of 1 to 10 nucleotides in one of the nucleotide sequences recited in SEQ ID nos. 1 to 7,
  (ii) addition of 1 to 10 nucleotides in one of the nucleotide sequences recited in SEQ ID nos. 1 to 7, and/or
  (iii) substitution of 1 to 3 nucleotides in one of the nucleotide sequences recited in SEQ ID nos. 1 to 7, c) a mixture of the oligonucleotides of a) and/or b), and the reverse primer is selected from the group consisting of:

d) an oligonucleotide that may be used as a primer, in particular a reverse primer, to amplify a nucleic acid region of a genital human papilloma virus having the nucleotide sequence 5'-ARY GGY TSY ARC CAA AAR TGR CT-3' (SEQ ID no. 7), wherein R=A or G, Y=C or T, and S=C or G, e) an oligonucleotide having a nucleotide sequence that is mutated relative to the oligonucleotide of d), and f) a mixture of the oligonucleotides of d) and e).

21. The nucleotide array and primer mixture kit of claim 20, wherein the control nucleic acid has a length and a GC content that corresponds to the length and the GC content of the amplification product that is obtained by means of an amplification process using the nucleic acid region of a genital human papilloma virus as the template and the primer pair of claim 20.

22. The nucleotide array and primer mixture kit of claim 8, wherein the hybridization control comprises at least one fourth oligonucleotide or nucleic acid molecule.

23. The nucleotide array and primer mixture kit of claim 22, wherein the hybridization control comprises at least 2 to 10 spots of the fourth oligonucleotide or nucleic acid molecule, and the spots have variously defined amounts of the fourth oligonucleotide or nucleic acid molecule.

24. The nucleotide array and primer mixture kit of claim 22, wherein the hybridization control comprises spots with a dilution series of the fourth oligonucleotide or nucleic acid molecule.

25. The nucleotide array and primer mixture kit of claim 8, wherein the sample control comprises at least one fifth oligonucleotide or nucleic acid molecule.

26. The nucleotide array and primer mixture kit of claim 25, wherein the fifth oligonucleotide or nucleic acid molecule is suitable for use as a probe for detecting the human ADAT1 gene.

27. The nucleotide array and primer mixture kit of claim 8, wherein the print control comprises at least one sixth oligonucleotide or nucleic acid molecule.

28. The nucleotide array and primer mixture kit of claim 1, wherein the oligonucleotides and nucleic acid molecules are embodied as DNA molecules, RNA molecules, PNA molecules, LNA molecules, or hybrid forms thereof.

29. The nucleotide array and primer mixture kit of claim 1, wherein the mixture of oligonucleotides as a forward primer includes:
  the oligonucleotide having SEQ ID no. 2;
  the oligonucleotide having SEQ ID no. 3;
  the oligonucleotide having SEQ ID no. 4;
  the oligonucleotide having SEQ ID no. 5; and
  the oligonucleotide having SEQ ID no. 6.

30. The nucleotide array and primer mixture kit of claim 1, wherein the mixture of oligonucleotides as a forward primer includes an equimolar mixture of each of the following:
  the oligonucleotide having SEQ ID no. 2;
  the oligonucleotide having SEQ ID no. 3;
  the oligonucleotide having SEQ ID no. 4;
  the oligonucleotide having SEQ ID no. 5; and
  the oligonucleotide having SEQ ID no. 6.

31. A nucleotide array and primer mixture, together as a kit, for detecting and/or identifying the genotype of a human papilloma virus contained in a biological sample:
  the nucleotide array comprising a solid carrier having a surface and at least one first oligonucleotide or nucleic acid molecule bound to the carrier surface that is suitable for use as a probe for testing the HPV gene E1 or a portion thereof to detect and/or identify a genital human HPV genotype, the at least one first oligonucleotide or nucleic acid molecule selected from the group consisting of:
  a) HPV genotype-specific oligonucleotides having the nucleotide sequences recited in SEQ ID Nos. 8 to 135,
  b) oligonucleotides that have a nucleotide sequence that is mutated relative to one of the oligonucleotides of a), namely, a deletion or addition of 1 to 10 nucleotides or a substitution of 1 to 3 nucleotides in one of the nucleotide sequences recited in a),
  c) oligonucleotides that have a nucleotide sequence that is complementary over its entire length to the nucleotide sequence of an oligonucleotide of a) or b),
  d) nucleic acid molecules comprising at least one region that has one of the nucleotide sequences recited in a) to c) and one or more additional regions having a total length of at least one nucleotide, and
  e) mixtures of the oligonucleotides of a) to c) and/or of the nucleic acid molecules of d); and the primer mixture comprising:
    (1) a mixture of oligonucleotides as a forward primer, the mixture including at least two oligonucleotides selected from the group consisting of (i) to (v):
      (i) an oligonucleotide having the nucleotide sequence 5'-CAR GCN AAA TAT KTR AAA GAT TGT G-3' (SEQ ID no. 2),
      (ii) an oligonucleotide having the nucleotide sequence 5'-CAR GCA AAA TAT GTW AAG GAT TGT G-3' (SEQ ID no. 3),
      (iii) an oligonucleotide having the nucleotide sequence 5'-CAR GCW AAA ATT GTA AAR GAT TGT G-3' (SEQ ID no. 4),
      (iv) an oligonucleotide having the nucleotide sequence 5'-CAA GCA AAA ATA GTA AAR GAC TGT G-3' (SEQ ID no. 5)
      (v) an oligonucleotide having the nucleotide sequence 5'-CAR GCA AAA TAT GTA AAA GAC TGT G-3' (SEQ ID no. 6),
    (2) an oligonucleotide as a reverse primer having the nucleotide sequence 5'- ARY GGY TSY ARC CAA AAR TGR CT-3' (SEQ ID no. 7), wherein R=A or G, W=T or A, K=T or G, I=inosine, N=A, T, G, or C, D=A, T, or G, Y=C or T, and S=C or G.

32. The nucleotide array and primer mixture kit of claim 31, wherein the mixture of oligonucleotides as a forward primer includes each of the oligonucleotides (i) through (v).

33. The nucleotide array and primer mixture kit of claim 31, wherein the mixture of oligonucleotides as a forward primer includes an equimolar mixture of each of the oligonucleotides (i) through (v).

* * * * *